United States Patent
Wu et al.

(10) Patent No.: US 8,969,530 B2
(45) Date of Patent: Mar. 3, 2015

(54) ANTI-CLATHRIN HEAVY CHAIN MONOCLONAL ANTIBODY FOR INHIBITION OF TUMOR ANGIOGENESIS AND GROWTH AND APPLICATION THEREOF

(71) Applicant: Academia Sinica, Taipei (TW)

(72) Inventors: Han-Chung Wu, Taipei (TW); Kuo-Hua Tung, New Taipei (TW)

(73) Assignee: Academia Sinica, Taipei (TW)

( * ) Notice: Subject to any disclaimer, the term of this patent is extended or adjusted under 35 U.S.C. 154(b) by 229 days.

(21) Appl. No.: 13/644,311

(22) Filed: Oct. 4, 2012

(65) Prior Publication Data

US 2013/0084298 A1    Apr. 4, 2013

Related U.S. Application Data

(60) Provisional application No. 61/543,118, filed on Oct. 4, 2011.

(51) Int. Cl.
| | | |
|---|---|---|
| C07K 16/00 | (2006.01) | |
| C12P 21/08 | (2006.01) | |
| G01N 33/53 | (2006.01) | |
| A61K 39/395 | (2006.01) | |
| A61K 39/00 | (2006.01) | |
| C07K 16/18 | (2006.01) | |
| C07K 16/30 | (2006.01) | |

(52) U.S. Cl.
CPC .............. *C07K 16/18* (2013.01); *C07K 16/303* (2013.01); *C07K 2317/73* (2013.01)
USPC ................... 530/388.1; 530/387.3; 530/387.7; 435/7.1; 424/130.1; 424/133.1; 424/138.1; 424/141.1; 424/155.1

(58) Field of Classification Search
None
See application file for complete search history.

(56) References Cited

U.S. PATENT DOCUMENTS 7,473,531 B1 * 1/2009 Domon et al. ................. 435/7.1

OTHER PUBLICATIONS

Ohata et al "Identification of a Function-Specific Mutation of Clathrin Heavy Chain (CHC) Required for p53 Transactivation" J. Mol. Biol. (2009) 394, 460-471.
Enari et al "Requirement of clathrin heavy chain for p53-mediated transcription" Genes Dev. 2006 20: 1087-1099.
Endo et al "Regulation of clathrin-mediated endocytosis by p53" Genes to Cells (2008)13, 375-386.
Kim et al (2011) "Endocytosis-Independent Function of Clathrin Heavy Chain in the Control Basal NF-kB Activation" PLoS One 6(2): e17158.
Tommaso et al "Diagnostic Accuracy of Clathrin Heavy Chain Staining in a Marker Panel for the Diagnosis of Small Hepatocellular Carcinoma" Hepatology, vol. 53, No. 5, 2011.
Joffre et al "A direct role for Met endocytosis in tumorigenesis" Nature Cell Biology vol. 13 No. 7, 2011.
Seimiya et al "identification of Novel Immunohistochemical Tumor Markers for Primary Hepatocellular Carcinoma; Clathrin Heavy Chain and Formiminotransferase Cyclodeaminase" Hepatology, vol. 48, No. 2, 2008.

* cited by examiner

*Primary Examiner* — Hong Sang
(74) *Attorney, Agent, or Firm* — Hsiu-Ming Saunders; Intellectual Property Connections, Inc.

(57) ABSTRACT

A purified monoclonal antibody, or an antigen-binding portion thereof, which specifically binds to human clathrin heavy chain (CHC) is disclosed. The antibody, or antigen-binding portion, thereof, exhibits at least one, two, three, four, five, six, seven, or all eight of the following properties: (a) specifically binds to pancreatic adenocarcinoma cells; (b) binding to the cell surface and cytosol of cancer cells and tumor blood vessels; (c) internalized by CHC-expressing cells; (d) inhibiting tumor growth, invasion ability, migration, and angiogenesis; (e) inducing apoptosis in cancer cells and human umbilical vein endothelial cells; (f) inhibiting tumor growth and tumor blood vessels in pancreatic cancer in vivo; (g) suppressing epidermal growth factor, transferrin, and VEGF internalizations by cancer cells; and (h) suppressing hypoxia-inducible factor-1α expression and vascular endothelial growth factor secretion. Methods for inhibiting tumor cell growth and/or angiogenesis, and detecting cancer in a subject is also disclosed.

18 Claims, 14 Drawing Sheets

FIG. 3
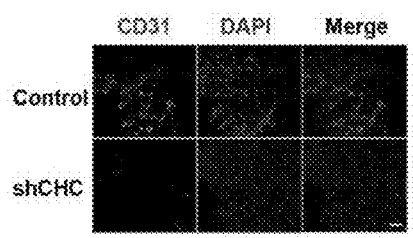
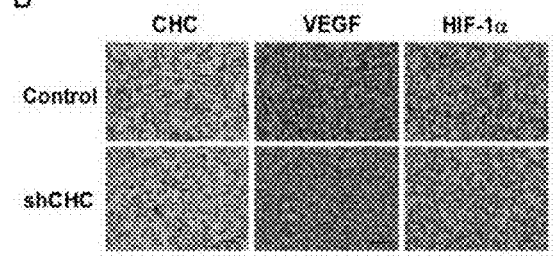
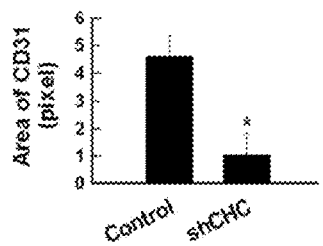
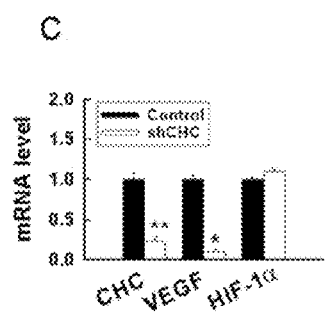
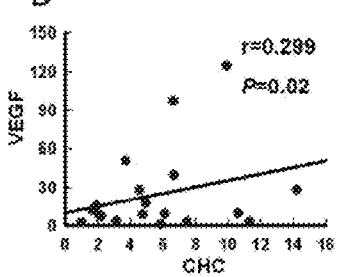
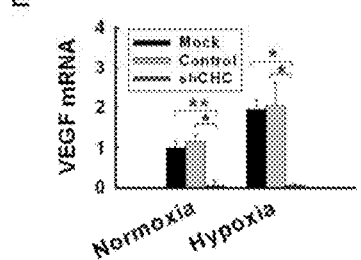
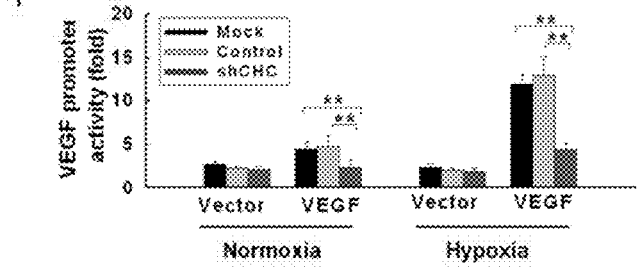
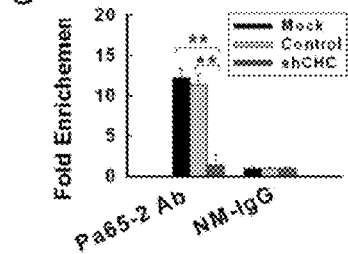
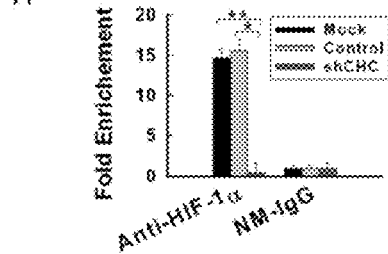

FIG. 8
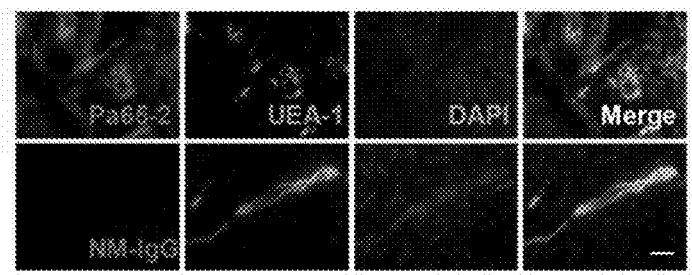
FIG. 9
A
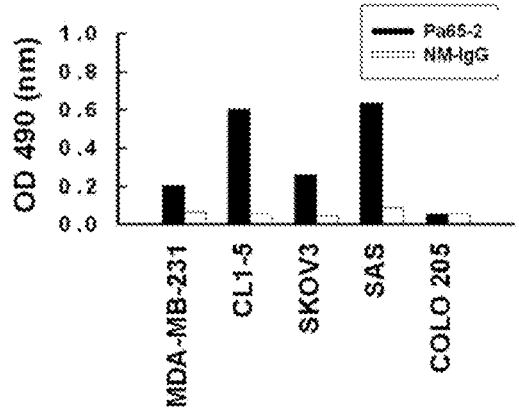
B
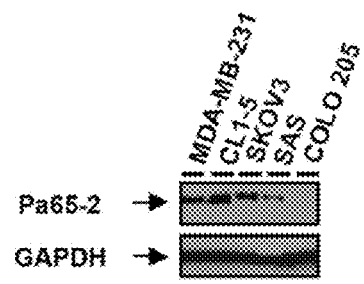

FIG. 10

FIG. 11
A
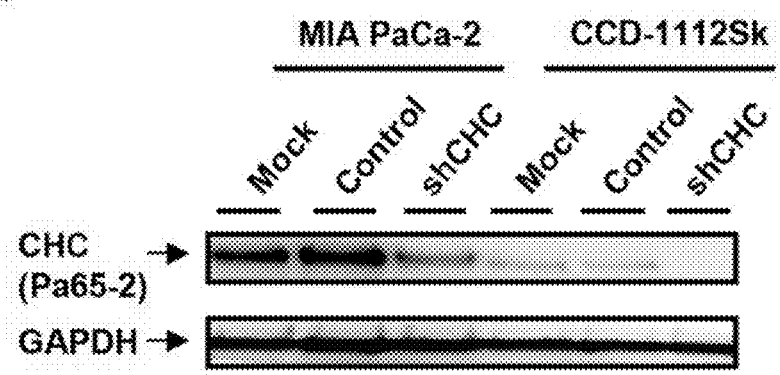
B
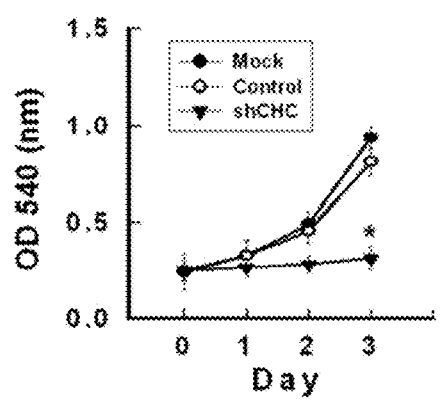
C
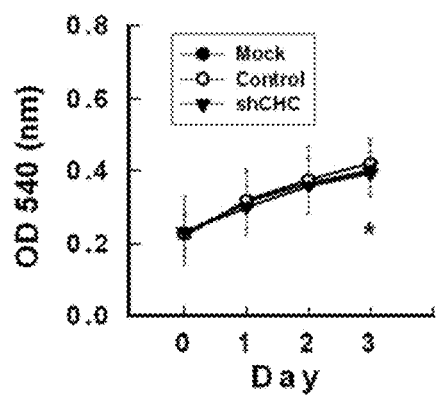

FIG. 15
A
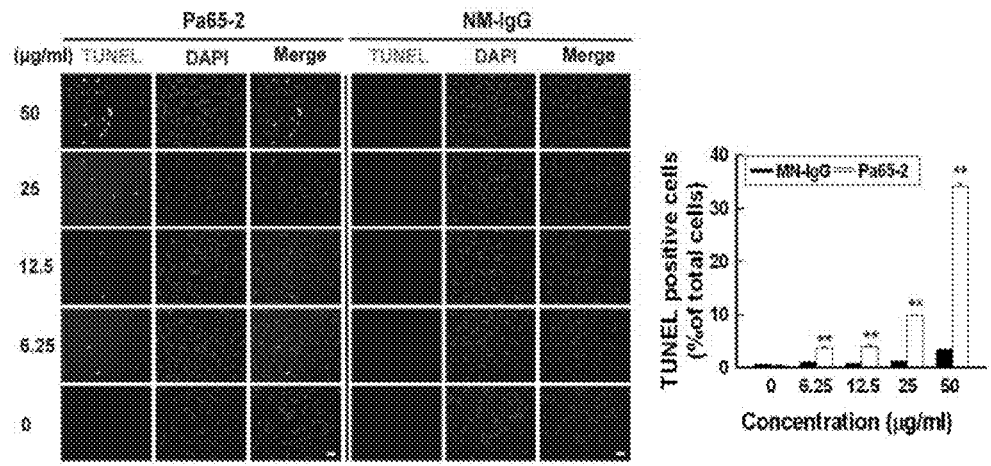
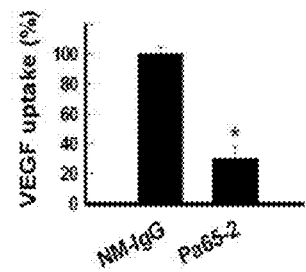
B

ANTI-CLATHRIN HEAVY CHAIN MONOCLONAL ANTIBODY FOR INHIBITION OF TUMOR ANGIOGENESIS AND GROWTH AND APPLICATION THEREOF

REFERENCE TO RELATED APPLICATION

The present application claims the priority to U.S. Provisional Application Ser. No. 61/543,118, filed Oct. 4, 2011, which is herein incorporated by reference in its entirety.

FIELD OF THE INVENTION

The present invention relates generally to anti-cancer agent, and more specifically to antibodies for treating cancers.

BACKGROUND OF THE INVENTION

About 95% of pancreatic cancer cases are adenocarcinomas. The overall five-year survival rate of pancreatic adenocarcinoma is about 5%. It is the fourth leading cause of cancer death in the United States. Pancreatic cancer often recurs after initial treatment despite the use of chemotherapy or radiation therapy. At present, there is no effective treatment for pancreatic cancer. The most commonly used medicine to treat pancreatic cancer is gemcitabine (GEM), a pyrimidine nucleoside drug, but it is only moderately effective.

Two monoclonal antibody (mAbs) drugs currently in clinical trial for targeted therapy against pancreatic cancers are cetuximab and bevacizumab, targeting epidermal growth factor receptor (EGFR) and vascular endothelial growth factor (VEGF), respectively. However, clinical trial data showed that using either cetuximab or bevacizumab, in combination with small molecule drugs had no significant improvement in the overall survival of pancreatic cancer patients.

Therefore, it is important to identify a suitable target for developing targeted therapy against pancreatic cancer.

SUMMARY OF THE INVENTION

In one aspect, the invention relates to a purified monoclonal antibody, or an antigen-binding portion thereof, which specifically binds to human clathrin heavy chain (CHC) comprising the amino acid sequence of SEQ ID NO: 1.

In another aspect, the invention relates to an isolated monoclonal antibody, or a binding fragment thereof. The isolated monoclonal antibody, or a binding fragment thereof comprises a heavy chain variable region and a light chain variable region, in which the heavy chain variable region comprises: (i) complementarity determining region 1 (CDR1) comprising SEQ ID NO: 4; (ii) complementarity determining region 2 (CDR2) comprising SEQ ID NO: 5; and (iii) complementarity determining region 3 (CDR3) comprising SEQ ID NO: 6; and the light chain variable region comprises: (i) CDR1 comprising SEQ ID NO: 7; (ii) CDR2 comprising SEQ ID NO: 8; and (iii) CDR3 comprising SEQ ID NO: 9.

In another aspect, the invention relates to a method for inhibiting tumor cell growth and/or tumor angiogenesis, which comprises administering to a subject, in need thereof a composition comprising the aforementioned purified monoclonal antibody, or antigen-binding portion thereof, and a pharmaceutically acceptable carrier.

Further in another aspect, the invention relate to a method for inhibiting tumor growth and/or tumor angiogenesis, which comprises: administering to a subject in need thereof a composition composing the aforementioned isolated monoclonal antibody, or binding fragment thereof, and a pharmaceutically acceptable carrier.

Further in another aspect, the invention relate to an isolated single-chain variable fragment comprising: (a) the heavy chain variable region (SEQ ID NO: 2) and the light chain variable .region (SEQ ID NO: 3) of the isolated antibody or binding fragment as aforementioned; and (b) a linker peptide connecting the heavy chain variable region (SEQ ID NO: 2) and the light chain variable region (SEQ ID NO: 3).

Further in another aspect, the invention relate to a method for detecting cancer in a. subject, which comprises: (a) applying the isolated monoclonal antibody, or binding fragment thereof, of claim 4 to a cell or tissue sample obtained from the subject; and (b) assaying the binding of the isolated monoclonal antibody, or binding fragment thereof to the cell or the tissue sample; and (c) comparing the binding with a normal control to determine the presence of the cancer in the subject, wherein the cancer expresses human clathrin heavy chain.

Yet in another aspect, the invention relates to a composition comprising: (a) the aforementioned isolated monoclonal antibody or binding fragment thereof; and (b) a pharmaceutically acceptable carrier.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 3 shows CHC regulation of VEGF expression in pancreatic cancer. (A) Expression of endothelial cell marker CD31 in CHC knockdown tumor sections by immunofluorescent staining (upper panel). Quantification of fluorescence intensity was performed using MetaMorph software (lower panel). Scale bar, 200 µm; Error bars denote ±SD. *P<0.05. (B) Immunohistochemical localization of CHC, VEGF and HIF1-α in tumor sections. Scale bar, 40 µm. (C) Quantitative RT-PCR analyses of CHC, VEGF and HIF-1α gene expressions in xenograft tumors. Gene expression levels were normalized to GAPDH signal. Error bars denote ±SD. *P<0.05; **P<0.01. (D) CHC and VEGF mRNA levels in samples obtained from 19 human pancreatic cancer patients were measured by quantitative RT-PCR analysis. Correlation between CHC and VEGF expression was evaluated by Spearman's analysis, (r=0.299; P=0.02). (E) Quantitative RT-PCR analysis of VEGF mRNA in CHC knockdown MIA PaCa-2 cells. Expression of VEGF was normalized to GAPDH. Error bars denote ±SD. *P<0.05; P<0.01. (F) Effect of CHC on activation of the VEGF promoter in MIA PaCa-2 cells after hypoxia. The cells were transfected with reporter plasmids and subjected to luciferase assay-Error bars denote ±SD. P<0.01. (G) and (H) Analysis of binding of CHC and HIF-1α on the VEGF promoter by chromatin immunoprecipitation (ChIP) analyses after hypoxia for 16 h. Specific primer sets for the VEGF promoter region containing two HIF-1α binding sites (−534 to −158) were used. A ChIP assay was performed using antibodies against (G) CHC (Pa65-2) and (H) HIF-1α. Normal mouse IgG was used as a negative control. Error bars denote ±SD.*P<0.05; **P<0.01.

FIG. 8 shows the results of immunofluorescent staining of Pa65-2 and Ulex europeus agglutinin-1 (UEA-1), which indicates they are co-localized. These results indicate Pa65-2 is also expressed in blood vessels of human pancreatic tumor mass (red, Pa65-2; green, UEA-1). Scale bar, 20 µm.

FIG. 9 shows binding activity of Pa65-2 against various cancer cell lines. (A) ELISA analysis of the binding activity of Pa65-2 in various cancer cell lines. NM-IgG was used as a control. (B) Western blot analysis of Pa65-2 in various cancer cell lines.

FIG. 10 shows the alignment of peptide sequences obtained from LC-nanoESI-MS/MS analysis of the Pa65-2 -target protein and the sequence of human CHC protein. The letters in bold and underlined represent the Pa65-2 -target protein sequences that match the sequences of human CHC protein (SEQ ID NO: 1).

FIG. 11 shows suppression of CHC expression had no effect on human skin fibroblast cell growth. (A) The results, of CHC knockdown were determined by Western blot analysis. MIA PaCa cells were used, as a control. (B) MIA PaCa-2 cells and (C) CCD-1112Sk cells proliferation was detected by MTT (3-(4,5-cimethylthiazol-2-yl)-2,5-diphenyl tetrazolium bromide) analysis. Error bars denote ±SD. *P<0.05.

FIG. 15 shows inhibition of endothelial cells growth in vitro by Pa65-2. (A) Immunofluorescent analysis of VEGF internalization in HUVECs after CHC inhibition by Pa65-2. HUVECs were pretreated with Pa65-2 or NM-IgG at 37° C., and subsequently incubated with or without VEGF (40 ng/ml) at 37° C. or 4° C. The cells were stained to detect antibodies against VEGF-A (red: Rhodamine staining) and for the nucleus using DAPI (blue). Scale bar, 50 µm. (B) Detection of Pa65-2 -induced apoptosis in HUVEC by TUNEL staining. Scale bar, 100 µm; Error bars denote ±SD. **P<0.01.

DETAILED DESCRIPTION OF THE INVENTION

Definitions

Figure 1:
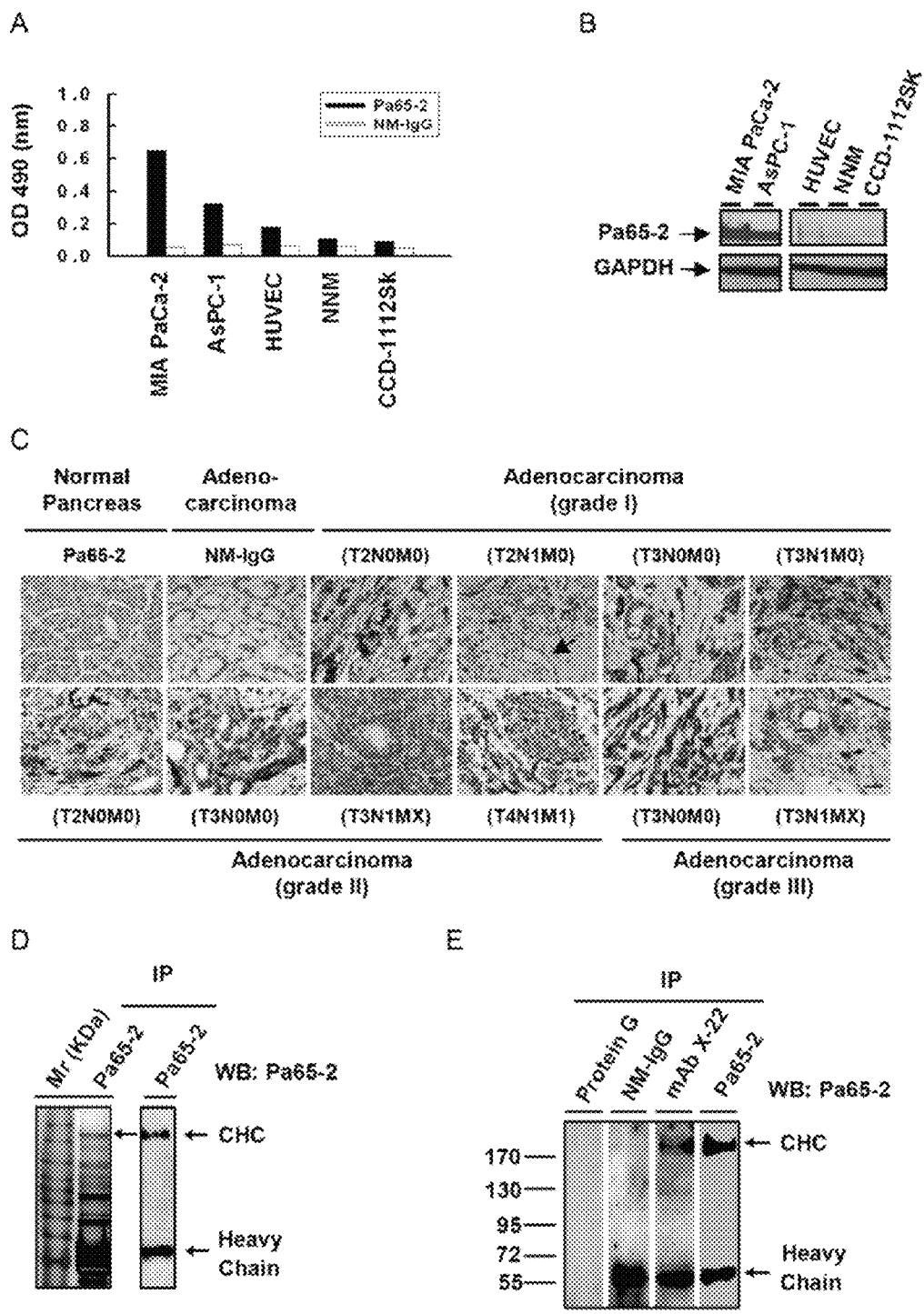
FIG. 1 shows generation and characterization of mAbs against pancreatic cancer. (A) ELISA and (B) Western blot analysis of the binding activity of Pa65-2 in pancreatic adenocarcinoma cell lines and various normal cell lines. NM-IgG was used as a control. (C) Immunohistochemistry analysis of Pa65-2 in human pancreatic cancer tissue array. The arrow indicates a blood vessel-like structure. Scale bar, 50 µm. (D) Purification of Pa65-2-targeted protein by immunoaffinity chromatography. Lane 1, molecular weight marker; lane 2, purified proteins from Pa65-2-conjugated affinity column; and lane 3, Western blot analysis of purified proteins from Pa65-2-conjugated affinity column. (E) MIA PaCa-2 whole-cell lysates were immunoprecipitated with Pa65-2 and anti-CHC and control antibodies followed by Western blot analysis.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

Abbreviations: mAb, monoclonal antibodies; CHC, clathrin Heavy Chain; HIF-1α, Hypoxia-inducible factor 1α; VEGF, vascular endothelial growth factor; NNM, Normal nasal mucosal; FACS, flow cytometric analysis; ELISA, Enzyme-linked immunosorbent assay; EMT, epithelial-mesenchymal transition; Quantitative Reverse Transcription Polymerase Chain Reaction (RT-PCR); ChIP, Chromatin Immunoprecipitation; GAPDH, glyceraldehyde-3-phosphate dehydrogenase; HUVEC, Human Umbilical Vein Endothelial Cells; IHC, immunohistochemistry; DFX, deferoxamine; EKE, hypoxia responsive element; UEA-1, Ulex europaeus 1 agglutinin; CDR, complementarity-determining region; LC-nanoESI-MS/MS, liquid chromatography-nano-electrospray ionization tandem mass spectrometry.

As used herein, "preparation" shall generally mean something prepared, manufactured, a substance especially prepared.

As used herein, the term "antibody" means an immunoglobulin (Ig) molecule or a fragment of an immunoglobulin molecule having the ability to specifically bind to a particular antigen. The Ig monomer is a "Y"-shaped molecule that consists of four polypeptide chains; two identical heavy chains and two identical light chains connected by disulfide bonds. The arms of the Y, for example, contain the site that bind antigen and, therefore, recognize specific foreign objects. This region of the antibody is called the Fab (fragment, antigen binding) region.

Antibodies are well known to those of ordinary skill in the science of immunology. As used herein, the term "antibody" means not only full-length antibody molecules but also fragments of antibody molecules retaining antigen binding ability. Such fragments are also well known, in the art and are regularly employed both in vitro and in vivo. In particular, as used herein, the term "antibody" means not only full-length immunoglobulin molecules but also antigen binding active fragments such as the well-known active fragments $F(ab')_2$, Fab, Fv, and Fd.

The fragment antigen-binding (Fab fragment) is a region on an antibody that binds to antigens. It is composed of one constant and one variable domain of each of the heavy and the light chain. The two variable domains bind the epitope on their specific antigens. Fc and Fab fragments can be generated in the laboratory. The enzyme papain can be used to cleave an immunoglobulin monomer into two Fab fragments and an Fc fragment. The enzyme pepsin cleaves below hinge region, so a $F(ab')_2$ fragment and a pFc' fragment is formed. The enzyme IdeS (Immunoglobulin degrading enzyme from *Streptococcus pyogenes*, trade name FabRICATOR™) cleaves IgG in a sequence specific manner at neutral pH. The $F(ab')_2$ fragment can be split into two Fab' fragments by mild reduction.

The variable domain of an antibody is referred to as the Fv region and is the most important region for binding to antigens.

The Fv fragment consists of the heavy chain variable domain (VH) and the light chain variable domain (VL) held together by strong noncovalent interaction. Thus, each Fv fragment contains one intact antigen-binding site and represents the minimal active fragment derivable from an antibody molecule.

The variable regions of the heavy and light chains can be fused together to form a single-chain variable fragment (scFv), which is only half the size of the Fab fragment, yet retains the original, specificity of the parent immunoglobulin.

It has been reported that "fully" human antibodies may avoid some of the side effects of humanized and chimeric antibodies. Two successful approaches were identified—phage display-generated antibodies and mice genetically engineered to produce more human-like antibodies. Phage display could be used such that variable antibody domains could be expressed on filamentous phage antibodies.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies. Such chimeric antibodies may be produced in which some or all of the FR regions of the antibody have been replaced by other homologous human PR regions.

Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et at, Nature, 321:522-525 (1986); Riechmann et al., Nature, 332:323-329 (1988): and Presta, Curr. Op. Steel Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries. The techniques of Cole et al. and Boerner et al. are also available for the preparation of human monoclonal antibodies (Cole et al., Monoclonal Antibodies and Cancer Therapy, Alan R. Liss, p. 77(1985) and Boerner et al., J. Immunol., 147(1) 86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807: 5,545,806; 5,569,825; 5,625,126; 5,633,425: 5,661,016. Such fully human or humanized monoclonal antibodies will have particular utility in that they will not evoke an immune response against the antibody itself See U.S. Pat. No. 7,622,113, which is herein incorporated by reference in its entirety.

The antibody may be labeled and may be immobilized on a solid support. The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

We have generated several mAbs recognizing pancreatic cancer cells. One of these mAbs, Pa65-2, can recognize clathrin heavy chain (CHC). Clathrin, encoded by the CLTC gene at 17q23.2, is a trimer of heavy chains (~190 kDa each), each paired with a light chain (25-27 kDa). The basic unit of its assembly is the triskelion, which has a flexible, three-armed polyhedral cage-like structure. Clathrin plays a crucial role in clathrin-mediated endocytosis (CME) pathway, a major route for membrane trafficking. It is involved in the ubiquitous uptake of ligand-receptor complexes, membrane transporters, and adhesion molecules. Clathrin also stabilizes the fibers of the spindle apparatus during mitosis. However, the main mechanism of CHC in tumorigenesis remains unknown.

We found that CHC may regulate the stability of the α subunit of hypoxia inducible factor-1 (HIF-1α). When cells are exposed to hypoxic conditions, HIF-1α is stabilized, which subsequently upregulates several downstream genes to promote cell survival in low-oxygen conditions. HIF-1α accumulation mediates cellular and systemic adaptive, responses to maintain oxygen homeostasis. It. also upregulates hypoxia-inducible genes, which are involved, in angiogenesis, erythropoiesis, energy metabolism as well as cell survival decisions in all metazoan species. In cancerous conditions, cells within rapidly growing solid tumors are exposed to chronic or intermittent hypoxia. Therefore, tumor cells encounter powerful selective pressure from hypoxia during their progression, invasion, and metastasis. An elevated expression of hypoxia-responsive proteins is a poor prognostic sign in many types of solid tumors, and the results from several studies suggest that agents acting directly or indirectly against the expression of HIF-1α have anticancer effects.

In the present study, it was found that CHC, which is associated with the HIF-1α, increases the protein's stability and facilitates its nuclear translocation, thereby regulating VEGF gene expression in cancer cells. The newly generated Pa65-2 inhibited tumor growth and angiogenesis, suggesting that this mAb can potentially be used to inhibit tumor angiogenesis and tumorigenesis in pancreatic cancer.

In one aspect, the invention relates to a purified monoclonal, antibody, or an antigen-binding portion thereof, which specifically binds to human clathrin heavy chain (CHC) comprising the amino acid sequence of SEQ ID NO: 1.

In one embodiment of the invention, the purified monoclonal antibody or antigen-binding portion thereof comprises: (a) a heavy chain variable region comprising the amino acid sequence of SEQ ID NO: 2; and (b) a light chain variable region comprising the amino acid sequence of SEQ ID NO: 3.

In another embodiment of the invention, the purified monoclonal antibody or antigen-binding portion thereof binds to cells selected from the group consisting of pancreatic cancer cells, breast cancer cells, lung cancer cells, ovary cancer cells, oral cancer cells, and tumor-associated endothelial cells.

In another aspect, the invention relates to an isolated monoclonal antibody, or a binding fragment thereof. The isolated monoclonal antibody, or a binding fragment thereof comprises a heavy chain variable region and a light chain variable region, in which the heavy chain variable region comprises; (i) complementarity determining region 1 (CDR1) comprising SEQ ID NO: 4; (ii) complementarity determining region 2 (CDR2) comprising SEQ ID NO: 5; and (iii) complementarity determining region 3 (CDR3) comprising SEQ ID NO: 6; and the light chain variable region comprises: (i) CDR1 comprising SEQ ID NO: 7; (is) CDR2 comprising SEQ ID NO: 8; and (iii) CDR3 comprising SEQ ID NO: 9.

In one embodiment of the invention, the isolated antibody or binding fragment comprises a heavy chain variable domain ($V_H$) SEQ ID NO: 2 and/or a light chain variable domain ($V_L$) SEQ ID NO: 3.

In another embodiment of the invention, the binding fragment comprises an Fv fragment of the antibody.

In another embodiment of the invention, the binding fragment comprises an Fab fragment of the antibody.

In another embodiment of the invention, the antibody is a fully human monoclonal antibody.

In another embodiment of the invention, the antibody is a humanized monoclonal antibody.

In another embodiment of the invention, the aforementioned anybody, or binding fragment thereof, binds to a cancer cell expressing clathrin heavy chain (CHC).

In another embodiment of the invention, the isolated antibody or binding fragment is labeled with a detectable compound or an enzyme.

In another embodiment of the invention, the isolated antibody or binding fragment is encapsulated within a liposome.

In another aspect, the invention relates to a method for inhibiting tumor cell growth and/or tumor angiogenesis, which comprises administering to a subject in need thereof a composition comprising the aforementioned purified monoclonal antibody, or antigen-binding portion thereof, and a pharmaceutically acceptable carrier.

Further in another aspect, the invention relate to a method for inhibiting tumor growth and/or tumor angiogenesis, which comprises: administering to a subject in need thereof a composition comprising the aforementioned isolated monoclonal antibody, or binding fragment thereof, and a pharmaceutically acceptable carrier.

In one embodiment of the invention, the tumor cell expresses clathrin heavy chain (CHC). In another embodiment of the invention, the tumor cell is selected from the group consisting of pancreatic cancer cells, breast cancer cells, lung cancer cells, ovary cancer cells, oral cancer cells, and tumor-associated endothelial cells.

Further in another aspect, the invention relate to an isolated single-chain variable fragment comprising; (a) the heavy chain variable region (SEQ ID NO: 2) and the light chain variable region (SEQ ID NO: 3) of the isolated antibody or binding fragment as aforementioned; and (b) a linker peptide connecting the heavy chain variable region (SEQ ID NO: 2) and the light chain variable region (SEQ ID NO: 3).

Further in another aspect, the invention relate to a method for detecting cancer in a subject, which comprises: (a) applying the isolated monoclonal antibody, or binding fragment thereof, of claim 4 to a cell or tissue sample obtained from the subject; and (b) assaying the binding of the isolated monoclonal antibody, or binding fragment thereof to the cell or the tissue sample; and (c) comparing the binding with a. normal control to determine the presence of the cancer in the subject, wherein the cancer expresses human clathrin heavy chain.

Yet in another aspect, the invention relates to a composition comprising; (a) the aforementioned isolated monoclonal antibody or binding fragment thereof and (b) a pharmaceutically-acceptable carrier.

Alternatively, the invention relates to a composition comprising: (a) the aforementioned purified monoclonal antibody or antigen-binding portion thereof; and (b) a pharmaceutically acceptable carrier.

In one embodiment of the invention, the composition further comprises an anticancer agent. The anticancer agent may be a small molecule drug including, but not limited to, germicitabine.

In another embodiment of the invention, the aforementioned isolated monoclonal antibody, or an antigen-binding portion thereof, exhibits at least one, two, three, four, five, six, seven, or all eight of the following properties: (a) specifically binds to pancreatic adenocarcinoma cells; (b) binds to the cell surface and cytosol. of cancer cells and tumor blood vessels; (c) is internalized by CHC-expressing cells; (d) inhibiting tumor growth, invasion ability, migration, and angiogenesis; (e) inducing apoptosis in cancer cells and human umbilical vein endothelial cells (HUVECs); (f) inhibiting tumor growth and tumor blood vessels in pancreatic cancer in vivo; (g) suppressing epidermal growth factor (EGF), transferrin (Tf), and VEGF internalizations by cancer cells; or (h) suppressing hypoxia-inducible factor-1α (HIF-1α) expression and vascular endothelial growth factor (VEGF) secretion.

EXAMPLES

Without intent, to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Cell Lines and Culture

Human pancreatic adenocarcinoma cell lines (MIA PaCa-2 and AsPC-1), human breast carcinoma cell lines (MDA-MB-231), human ovarian cancer cell lines (SKOV3), human colon cancer cell lines (COLO 205), and a human skin fibroblast cell line (CCD-1112Sk), were purchased from American Type Culture Collection (ATCC®), These cells were cultured in accordance with cell bank protocols and had been passaged for less than 6 months after resuscitation. Normal nasal mucosal (NNM) epithelia were a primary culture derived from a nasal polyp. Human umbilical vein endothelial cells (HUVECs) were purchased (LONZA™) and grown in EBM-2 medium (LONZA™). The cell lines, including were purchased from American Type Culture Collection (ATCC®), Human oral cancer cell lines (SAS) were obtained from the Japanese Cancer Research Resources Bank. These cells were cultured by cell bank protocols and had been passaged for fewer than 6 months after resuscitation.

Generation of Monoclonal Antibodies

Monoclonal antibodies against MIA PaCa-2 were generated following a standard procedure with slight modifications. Briefly, female BALB/cJ mice were immunized intraperitoneally with MIA PaCa-2 four times at 3-week intervals. On day 4 after the final boost, splenocytes were harvested from the immunized mouse spleen and fused with NSI/1-Ag4-1 myeloma cells by 50% polyethylene glycol (GIBCO™). Those hybridomas, positive for MIA PaCa-2 but negative for NNM, were then subcloned by limited dilution and preserved in liquid nitrogen. Ascites were produced in pristane-primed BALB/cJ mice and mAbs purified with protein G Sepharose 4G gel (GE).

Identification of the Target Protein of Pa65-2

MIA PaCa-2 cell lysates were purified by protein G sepharose (GE), coupled with Pa65-2 and eluted with elution buffer. The eluates were separated by SDS-PAGE. The band of interest was cut from the gel, reduced with dithioerythreitol (DTE) alkylated with iodoacetamide (IAA) and digested with trypsin for 16 h at 37° C. The digested peptides were analyzed by LC-MS/MS sequencing in the Core Facility for Proteomics and Structural Biology Research at Academia Sinica (Taipei).

Immunoprecipitation and Immunoblotting Assay

Cells were extracted with RIPA buffer and the supernatants were immunoprecipitated using either anti-CHC antibody, Pa65-2, mAb X-22 (Affinity), or anti-HIF-1α antibody (BD), then analyzed by immunoblotting. The signals were developed using enhanced chemiluminescence reagents (ECL) (Thermo).

Enzyme-Linked Immunosorbent Assay and Flow Cytometric Analysis

Cells were cultured in 96-well polystyrene plates for 3 days and then fixed with 2% paraformaldehyde. After blocking and washing twice with PBS/0.1 % Tween 20 (PBST0.1), the hybridoma supernatants were added and the plates were incubated for 2 h at room temperature. This was followed by washing and incubating with horseradish peroxidase (HRP)-conjugated goat anti-mouse IgG for 1 h. The colorimetric reaction was developed with the substrate ortho-phenylenediamine (OPD) according to the manufacturer's instructions (Sigma), and was stopped by adding 3 N HCl. Absorbance at 490 nm was measured using a microplate reader. Each control and test group was tested in triplicate. Each experiment was repeated at least three times. To analyse binding, cells ($1 \times 10^5$ cells per tube) were prepared, washed, centrifuged, and resuspended in 100 μl of PBS/1% FCS containing Pa65-2 or NM-IgG. Cells were incubated at 4° C. for 1 h, washed twice with PBS/1% FCS and stained with fluorescent isothiocyanate (FITC)-labeled goat anti-mouse IgG at 4° C. for 20 min. The stained cells were washed twice and fluorescence signals were measured using a FACScan (BD). At least $5 \times 10^3$ cells were acquired by list mode, measurements were performed on a single cell basis, and were displayed as frequency distribution histograms or dot histograms.

MTT assay

Cells were cultured in 96-wells plates. To reduce cancer growth, the cells were culture in Dulbecco's modified Eagle's medium (DMEM) containing 50 μg/ml Pa65-2 or NM-IgG. After incubating for 0, 1, 2, 3 days, the cells were subjected to an MTT assay. The absorbance was determined with a microplate reader at 540 nm. Each assay was repeated for three times.

Inhibition of HUVEC Internalization by Pa65-2

HUVEC were washed with serum-free medium, incubated in 1% BSA in serum-free medium at 37° C., and pretreated with Pa65-2 or NM-IgG (50 μg/ml) at 37° C. They were then incubated with or without VEGF-A (40 ng/ml) at 37° C. or 4° C. After cells were washed, fixed and made permeable. The permeable cells were incubated with anti VEGF-A antibody (A-20, Santa Cruz). Finally, cells were stained using Rhodamine-conjugated secondary antibodies.

Cell Proliferation Analysis and Invasion Assays

RT-CES (ACEA), a microelectronic cell sensor system, was used to count tire number of living cells. Cells ($5 \times 10^3$) were seeded into each sensor-containing well in microliter plates. The electronic sensors provided a continuous (every 6 h), quantitative measurement of the cell index in each well. Cell growth was measured for 72 h, and cell indices for each well were recorded at all time points. Cell invasion was assayed in 24-well Biocoat Matrigel invasion chambers (8 µm; Millipore) according to the manufacturer's directions. Cells were counted under a microscope in five predetermined fields. Assays were performed in triplicate.

shRNA Transfection and Luciferase Reporter Gene Assays

Lentiviruses (pLKO.1) containing the CHC shRNA ID TRCN0000007984 (Academia Sinica, Taipei) and pLKO.1 empty vector controls were generated and used to infect MIA PaCa-2 cells. The stable transfectants were established by puromycin selection. The VEGF reporter plasmids contains nucleotides −2274 to +379 of the VEGFgene inserted into luciferase reporter pGL2-Basic (PROMEGA™) as previously described (Forsythe et al (1996) Activation of vascular endothelial growth factor gene transcription by hypoxia-inducible factor 1. *Mol Cell Biol*, 16, 4604-13), VEGF promoter primer sequences are presented in Table 3. Luciferase reporter gene assays were conducted using the Renilla Luciferase Assay System (PROMEGA™) according to the manufacturer's directions. The Renilla luciferase was constructed for normalization of transfection efficiency. Relative light units were calculated as the ratio of Firefly luciferase to Renilla luciferase activity (normalized luciferase activity).

Quantitative Reverse Transcription Polymerase Chain Reaction (RT-PCR)

RNA extractions were performed using the RNeasy Mini kit (QIAGEN,) according to the manufacturer's instructions. First strand cDNA was synthesized from 1.0 µg of total RNA by SuperScript III reverse transcriptase (INVITROGEN™). CLTC, VEGF, HIF-1α, erythropoietin (EPO), platelet-derived growth factor-β (PDGF-β) and glyceraldehyde-3-phosphate dehydrogenase (GAPDH) primers sequences are presented in Table 4. Real-time PCR was performed using a LightCycler 480 System (Roche). Cycling temperatures were as follows: denaturing 94° C., annealing 60° C., and extension 70° C. Data were normalized by the expression level of GAPDH in each sample.

Hypoxia Assay

For hypoxia experiments, MIA PaCa-2 cells were grown in a Ruskinn Hypoxic Chamber (APM-50D, 18 Astec, Japan) and treated with either 1% $O_2$, 5% $CO_2$ for 18 h, or given DFX, deferoxamine (100 µM, Sigma) treatment for 5 or 16 h. For proteasome inhibitor treatment, MG132 (10 µM, Sigma) was added to culture medium then incubated 5 to 17 h.

Chromatin Immunoprecipitation (ChIP)

The protocol for chromatin immunoprecipitation (ChIp) has been described previously. Briefly, control and shCHC-expressing MIA PaCa-2 cells were fixed with 1% formaldehyde, lysed in lysis buffer, sonicated, and clarified by centrifugation. The supernatant was immunoprecipitated with anti-CHC, anti-HIF-1α (Abcam) or NM-IgG (Sigma) antibodies. The precipitates were then amplified by the LightCycler 480 System. The relative abundance of specific sequences in immunoprecipitated DMA was determined using the $\Delta\Delta C_1$ method with $C_1$ obtained for total extracted DNA (Input DNA) as a reference value. The amount of immunoprecipitated target was quantified by real-time PCR, and the value of immunoprecipitated target was calculated as the ratio of IP DNA to the total amount of input DNA used for the immunoprecipitation (IP/input) to obtain relative-fold enrichment value. ChIP primers sequences are presented in Table 5.

Immuno-Electron Microscopy

Cells were gently scraped out of the flasks using a cell scraper (Costar) and fixed in paraformaldehyde and glutaraldehyde. Following fixation, cell pellets were washed with buffer and 30% glycerol and gently agitated overnight at room temperature. Cells were subjected to freeze substitution in an AFS (Leica), in which they were dehydrated by methanol at −91° C. for 4-5 days. Cells were later warmed to −50° C., embedded in Lowicryl HM20, and polymerized at −50° C. by UV. Ultrathin sections of 90 nm thickness were obtained using an Ultracut UC7 (Leica). The sections were incubated with the Pa65-2 mouse IgG or anti-HIF-1α rabbit IgG. The secondary antibodies (Jackson), goat anti-mouse IgG (F(ab')$_2$ fragment) conjugated with 18 nm gold particles, or goat anti-rabbit IgG (F(ab')$_2$ fragment) conjugated with 12 nm gold particles, were then applied to their respective sections. Finally, the sections were stained with uranyl acetate and lead citrate, and examined by TEM (Hitachi).

Inhibition of Cell Internalization by Pa65-2

EGF and Tf uptake assays were carried out using a fluorescence-based approach, as previously described (26). Cells were washed with serum-free medium, incubated in 1% BSA in serum-free medium at 37° C., and pretreated with Pa65-2 or NM-IgG (50 µg/ml) at 37° C. They were then incubated with or without Alex 555-EGF (1 µg/ml, INVITROGEN™) or Alex 555-transferrin (50 µg/ml) at 37° C. or 4° C. The cells were imaged using a Leica TCS SP confocal microscope (Leica).

Immunofluorescent Staining

Cells were incubated with anti-Pa65-2 and anti-HIF-1α antibodies, and then with FITC- or Rhodamine-conjugated secondary antibodies (Jackson). Images were captured by confocal microscopy (Leica).

Apoptosis Assay

Apoptosis of cultured cells was verified through the detection of caspase activity using sulforhodamine FLICA apoptosis detection kit (Immunochemistry Technologies). Cells in 96-well culture plates were treated with Pa65-2 or NM-IgG for 24 h. After incubating with FLICA, cells was read at ex/era of 550/595 nm with fluorescence plate reader (Molecular Devices).

Animal Models

All animal experiments were performed as per the guidelines of the National Laboratory Animal Center. The protocol was approved by the Committee on the Ethics of Animal Experiments of Academia Sinica (Taipei). A xenograft model was generated by injecting NOD/SCID mice with MIA PaCa-2 cells transduced with either CHC shRNA or control vector. The two kinds of transduced cells were injected into different lateral sides of the hind limbs of eight animals at the same time. For analysis of antitumor efficacy of Pa65-2, NOD/SCID mice bearing MIA PaCa-2-derived pancreatic cancer xenografts (~50 mm$^3$) were intravenously injected in the tail vein with Pa65-2, or gemcitabine, or NM-IgG, or equivalent volumes of PBS. Tumors were measured by calipers every three days, and mice were observed routinely for weight loss as a symptom of drug toxicity. The tumor volumes were calculated as length×(width)$^2$×0.52. Animals were treated following the guidelines established by Academia Sinica (Taipei).

CD31 Staining and Terminal Deoxynucleotidyl Transferase-Mediated dUTP Nick End Labeling (TUNEL) Assay CD31 staining and TUNEL assays were carried out as described previously. The slides were then visualized under a fluorescent microscope and analyzed with MetaMorph software.

Analysis of Tissue Samples

The human pancreatic cancer gene expression arrays (Origene) were analyzed by an ABI9600 thermocycler (Applied Biosystems). Tissue arrays were purchased from Pantomics Inc. Tissue sections were stained with antibodies specific for CHC (Pa65-2), VEGF (GeneTex), HIF-1α (Millipore), NM- IgG, and UEA-1-FITC (Vector). Quantification of DAB intensity was by HistoQuest software (TissueGnostics). The protocol was approved by the institutional Review Board of Human Subjects Research Ethics Committee of Academia Sinica (Taipei).

cDNA Synthesis and Amplification of Variable Region

Total mRNA was extracted from Pa65-2-producing hybridoma cells using the FastTrack mRNA isolation kit (INVITROGEN™). The cDNA synthesis was based on Orlandi et al. (1989) "Cloning immunoglobulin variable domains for expression by the polymerase chain reaction" *Proc Natl Acad Sci USA*, 86, 3833-7. A reaction mixture containing 10 μg of mRNA, 20 pmol of VH1FOR primer or VK1FOR primers sequences are presented in Supplementary Table 2, 250 μM of each dNTP, 50 mM Tris-HCl pH 8.3, 140 mM KCl, 10 mM MgCl2, 10 mM dithiothreitol, and 20 units of RNAsin (PHARMACIA™/LKB Biotechnology) was heated at 70° C. for 10 min and cooled. Reverse transcriptase (Anglian Biotec) was added and the reaction incubated at 42° C. for 1 hr. For amplification by Taq DMA polymerase (PROMEGA™), a reaction mixture was made containing 5 μl of the c-DNA-RNA hybrid, 25 pmol of primers VH1FOR or VK1FOR and VH1BACK or VK1BACK primers sequences are presented in Supplementary Table 2. 250 μM of each dNTP, 67 mM Tris chloride (pH 8.8), 17 mM (NH4)2SO4, 10 mM MgCl2, 200 μg of gelatine per ml, and 2 units of Taq DNA polymerase PCR was performed for 45 cycles (1', 95° C.; 1', 55° C.; 2', 72° C.) followed by gel purification. The PCR products were then cloned into TA cloning vector pCR2.1 (INVITROGEN™) according to the manufacturer's protocol and the vector was transfected into the DH5α strain of *Escherichia coli* (GIBCO BRL™) and sequenced.

Statistical Analyses

Statistical analyses were done using unpaired Student's t-tests where appropriate. *,p<0.05,**,p<0.01 were considered significant.

Enzyme-linked Immunosorbent Assay and Flow Cytometric Analysis $3 \times 10^3$ cells were cultured into each well of 96-well polystyrene plates for 3 days and fixed with 2% paraformaldehyde. Alter blocking and washing twice with PBS/0.1% Tween 20 (PBST0.1), the hybridoma supernatants were added and the plates were incubated for 2 hr at room temperature. This was followed by washing and incubation with horseradish peroxidase (HRP)-conjugated goat anti-mouse IgG for 1 hr. The colorimetric reaction was developed with the substrate ortho-phenylene-diamine (OPD) according to manufacturer's instructions (Sigma, St. Louis, Mo.), and was stopped by adding 3 N HCl. Absorbance at 490 nm was measured using a microplate reader. Each control and test group was tested in triplicate. Each experiment was repeated at least three times. To analyse binding, cells ($1 \times 10^5$ cells per tube) were prepared, washed, centrifuged, and resuspended in 100 μl of PBS/1% PCS containing Pa65-2 or NM-IgG. Cells were incubated at 4° C. for 1 hr, washed twice with PBS/1% FCS and stained with fluorescent isothiocyanate (FITC)-labeled goat anti-mouse IgG at 4° C. for 20 min. The stained cells were washed twice and fluorescence signals were measured using a FACScan (BD Biosciences, San Jose, Calif.), At least $5 \times 10^3$ cells were acquired by list mode, measurements were performed on a single cell basis, and were displayed as frequency distribution histograms or dot histograms.

Quantitative Reverse Transcription Polymerase Chain Reaction (RT-PCR)

RNA extractions were performed using the RNeasy Mini kit (QIAGEN, Valencia, Calif.) according to the manufacturer's instructions. First strand cDNA was synthesized from 1.0 μg of total RNA by Superscript III reverse transcriptase (INVITROGEN™, Carlsbad, Calif.). The primers used for PCR amplification were: GAPDH-F, 5'-CTTCACCACCATG-GAGGAGGC-3' (SEQ ID NO: 30); GAPDH-R, 5'-GGCATGGACTGTGGTCATGAG-3' (SEQ ID NO: 31); and CLTC-F, 5'-GACAAAGGTGGATAAATTAGATGC-3' (SEQ ID NO: 20); CLTC-R, 5'-TAAACAATGGGTTGT-GTCTCTGTA-3' (SEQ ID NO: 21). Real-time PCR was performed using a LightCycler 480 System (Roche, Indianapolis, Ind.). Cycling temperatures were as follows: denaturing 94° C., annealing 60° C., and extension 70° C. Data were normalized by the expression level of GAPDH in each sample.

cDNA Synthesis and Amplification of Variable Region

Total mRNA was extracted from Pa65-2-producing hybridoma cells using the FastTrack mRNA isolation kit (INVITROGEN™, Carlsbad, Calif.). The cDNA synthesis was based on Orlandi et al. (1989) "Cloning immunoglobulin variable domains for expression by the polymerase chain reaction" *Proc Natl Acad Sci USA*, 86, 3833-7. A reaction mixture containing 10 μg of mRNA, 20 pmol of VH1FOR primer 5'-d(TGAGGAGACGGTGACCGTGGTCCCTTG-GCCCCAG-3' (SEQ ID NO: 36) or VH1FOR primer 5'-d (GTTAGATCTCCAGCTTGGTCCC-3' (SEQ ID NO: 37), 250 μM of each dNTP, 50 mM Tris-HCl pH 8.3, 140 mM KCl, 10 mM MgCl$_2$, 10 mM dithiothreitol, and 20 units of RNAsin (PHARMACIA™/LKB Biotechnology, Inc., Piscataway, N.J.) was heated at 70° C. for 10 min and cooled. Reverse transcriptase (Anglian Biotec, Colchester, U.K.) was added and the reaction incubated at 42° C. for 1 hr. For amplification by Taq DNA. polymerase (PROMEGA™, Madison, Wis., USA), a reaction mixture was made containing 5 μl of the cDNA-RNA hybrid, 25 pmol of primers VH1FOR or VH1FOR and VH1BACK 5'-d(AGGTSMARCTGCAG-SAGTCWGG-3' (in which S=C or G, M=A or C, R=A or G, and W=A or T) (SEQ ID NO: 38) or VK1BACK 5'-d(GA-CATTCAGCTGACCCAGTCTCCA-3' (SEQ ID NO: 39) as appropriate, 250 μM of each dNTP, 67 mM Tris chloride (pH 8.8), 17 mM (NH4)$_2$SO$_4$, 10 mM MgCl$_2$, 200 μg of gelatine per ml, and 2 units of Taq DNA polymerase. PCR was performed for 45 cycles (1', 95° C.; 1', 55° C.; 2', 72° C.) followed by gel purification, The PCR products were then cloned into TA cloning vector pCR2.1 (INVITROGEN™, Carlsbad, Calif.) according to the manufacturer's protocol and the vector was transfected into the DH5α strain of *Escherichia coli* (GIBCO BRL™, Gaithersburg, Md., USA) and sequenced.

Wound Scratch Assay $1 \times 10^5$ CL1-5 cells were plated onto tissue culture dishes. After 24 hr incubation, the cells were scratched in a standardized manner with a plastic apparatus to create a cell-free zone in each well, 2 mm in width. The cells were then incubated for 14 hr at 37° C. Migration of the cells into the scratch was observed at time points of 7 hr and 14 hr.

Results

Generation and Characterization of mAbs Against Pancreatic Cancer

To obtain a potential target for pancreatic adenocarcinoma therapy, BALB/cJ mice were immunized with MIA PaCa-2 cells. More than 6000 hybridoma clones were obtained. Supernatants from each fusion well were then tested for the production of specific antibodies against MIA PaCa-2 antigens by ELISA assay. Sixteen clones that exhibited higher reactivities against MIA PaCa-2 cells were selected (data not shown). One of these monoclonal antibodies, Pa65-2, was found to specifically recognize MIA PaCa-2 cells but not normal nasal mucosa (NNM) cells, as confirmed by ELSA, flow cytometry, and immunofluorescent analyses (FIGS.

Figure 7:
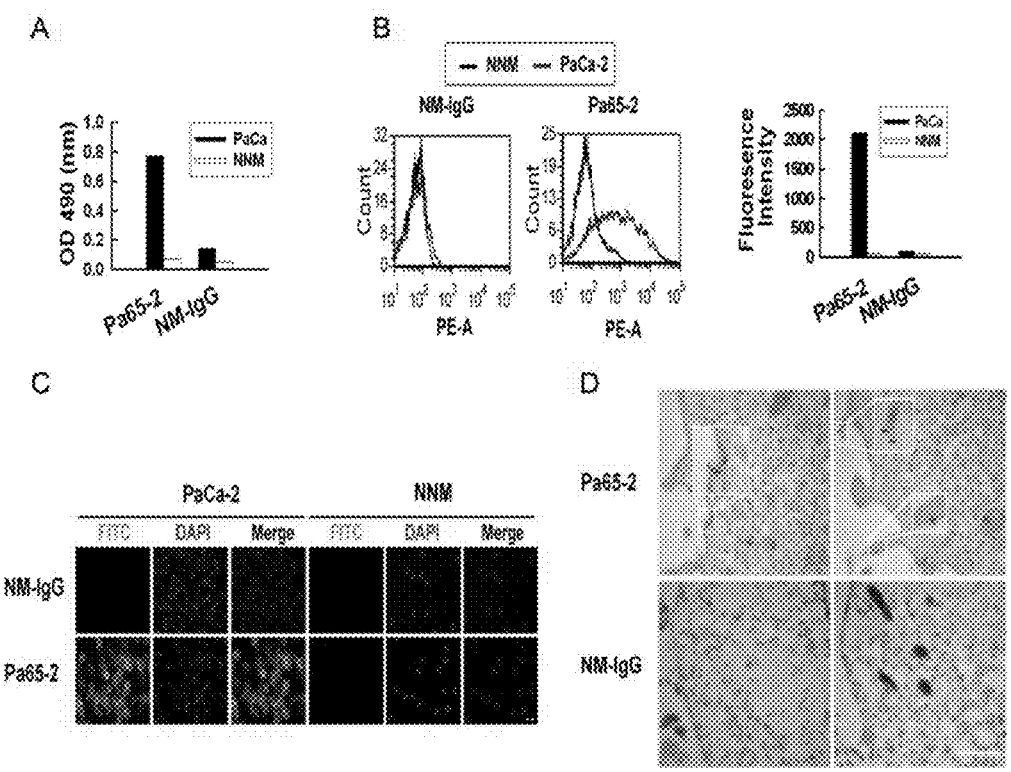
FIG. 7 shows the results of determination of the binding activities of Pa65-2 on MIA PaCa-2 cells. (A) Pa65-2 shows high affinity against MIA PaCa-2 cells by ELBA. Normal mouse IgG (NM-IgG) was used for negative control. (B) Flow cytometric analysis of Pa65-2 binding activity on MIA PaCa-2 and NNM (left panel) cells, fluorescent intensity indicates the binding activity of Pa65-2 on cells (right panel), (C) Immunofluorescent analysis of Pa65-2 localization in MIA PaCa-2 and NNM cells. Scale bar, 50 µm. (D) Pa65-2 shows high affinity against MIA PaCa-2 cell membrane and cytosol by labeling immuno-electron microscopy. Normal mouse IgG (NM-IgG) was used, for negative control. Scale bar. 500 nm.

7A-C). Immuno-electron microscopy showed cellular localization of Pa65-2 on the plasma membrane of MIA PaCa-2 cells (FIG. 7D). Pancreatic adenocarcinoma cell lines, MIA PaCa-2 and AsPC-1, and normal cell lines, HUVEC, NNM, and CCD-1112Sk, were screened by ELISA and Western blot analyses to characterize the binding property of Pa65-2. In general, Pa65-2 had strong binding affinity to pancreatic cancers cell lines (FIGS. 1A-B).

All 46 specimens of pancreatic cancer tissues were positively stained by Pa65-2, while two normal pancreatic tissues were not, as shown by the pancreatic cancer tissue arrays (FIG. 1C and Table 2), Notably; the target antigen of Pa65-2 is present not only in tumor tissues but also in blood vessel-like structures (FIG. 1C, arrow). Immunofluorescent analysis further confirmed that the antigen of Pa65-2 was colocalized with the endothelial cell marker Ulex europeus agglutinin-1 (UEA-1) in the blood vessels of human pancreatic cancer tissues (FIG. 8). Pa65-2 can also bind to other types of cancer cell lines, including MDAMB-231 (breast cancer), CL1-5 (lung cancer), SKOV3 (ovary cancer) and SAS (oral cancer), as shown by ELISA and Western blot analysis (FIG. 9).

Figure 2:
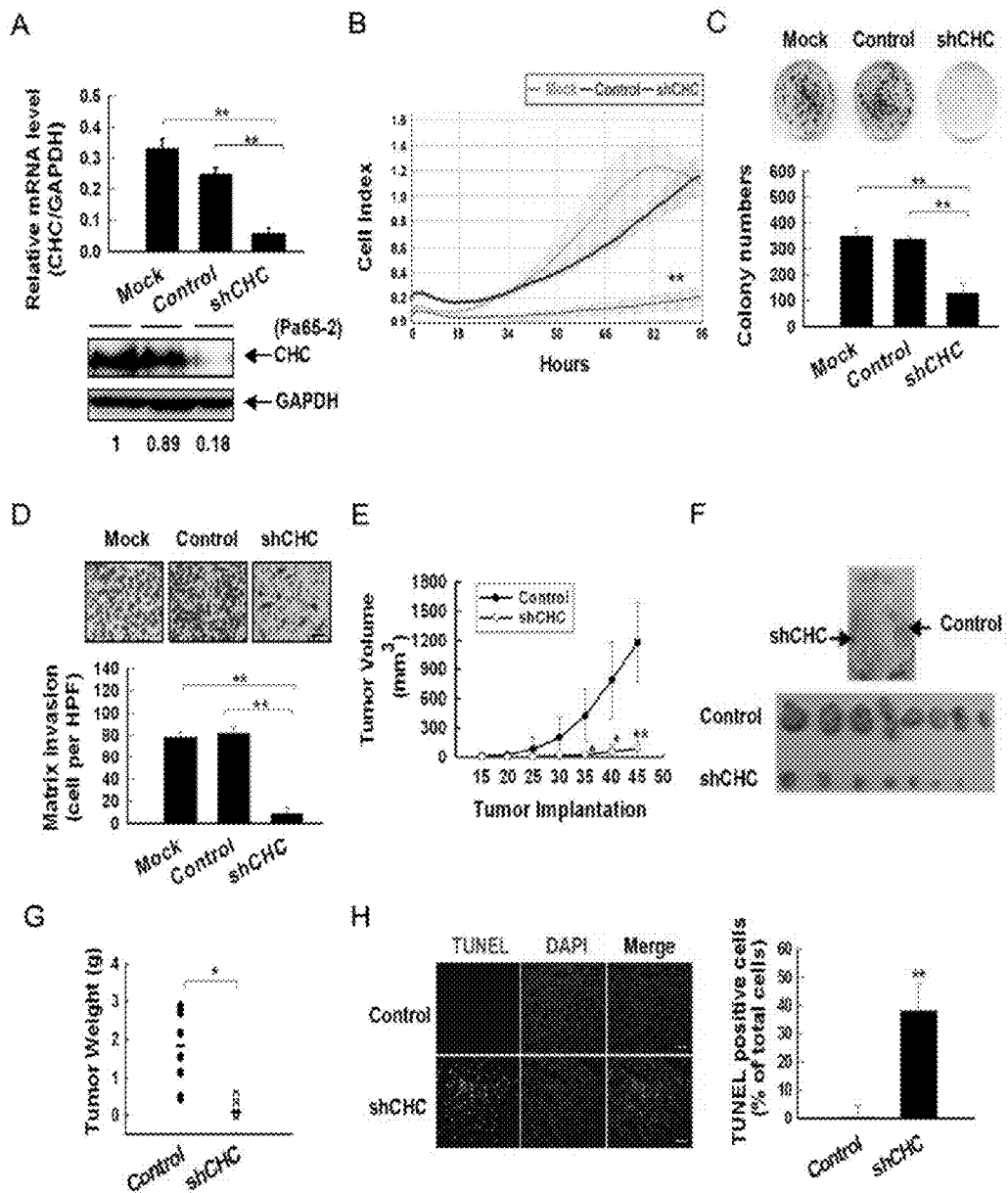
FIG. 2 shows inhibition of pancreatic cancer growth by suppressing CHC expression, (A) The results of CHC knockdown were determined by quantitative RT-PCR (upper panel) and Western blot analysis (lower panel). The band signal of CHC was normalized to GAPDH. Error bars denote±standard deviation (SD). P<0.01. (B) A microelectronic cell sensor system analysis of cell proliferation in mock, control vector-and shCHC-transfected MIA PaCa-2 cells. Error bars denote ±standard deviation (SD). P<0.01. (C) Colony formation potential of MIA PaCa-2 cells. Representative images are shown in the upper panel. Error bars denote ±SD. P<0.01. (D) Knockdown of CHC expression reduced invasion. Scale bar, 40 µm; Error bars denote ±SD. P<0.01. (E) Eight NOD/SOD mice were injected s.c. ($1 \times 10^7$ cells) in the lateral portion of the hind limb, right side with, the control vector-transduced MSA PaCa-2, and left side with the CHC shRNA-transduced MIA PaCa-2. The tumors were measured with calipers every five days, and tumor volume was calculated as length×(width)²×0.52. Error bars denote ±SD. *P<0.05; **P<0.01. (F) Representative images of tumor-hearing mice (upper panel) and tumor burden (lower panel) are shown. (G) Tumor weight was measured. Error bars denote ±SD. *P<0.05. (H) Detection of apoptosis induced by CHC shRNA in MIA PaCa-2 cells by TUNEL staining. Scale bar, 200 µm; Error bars denote ±SD. **P<0.01.
Figure 10:
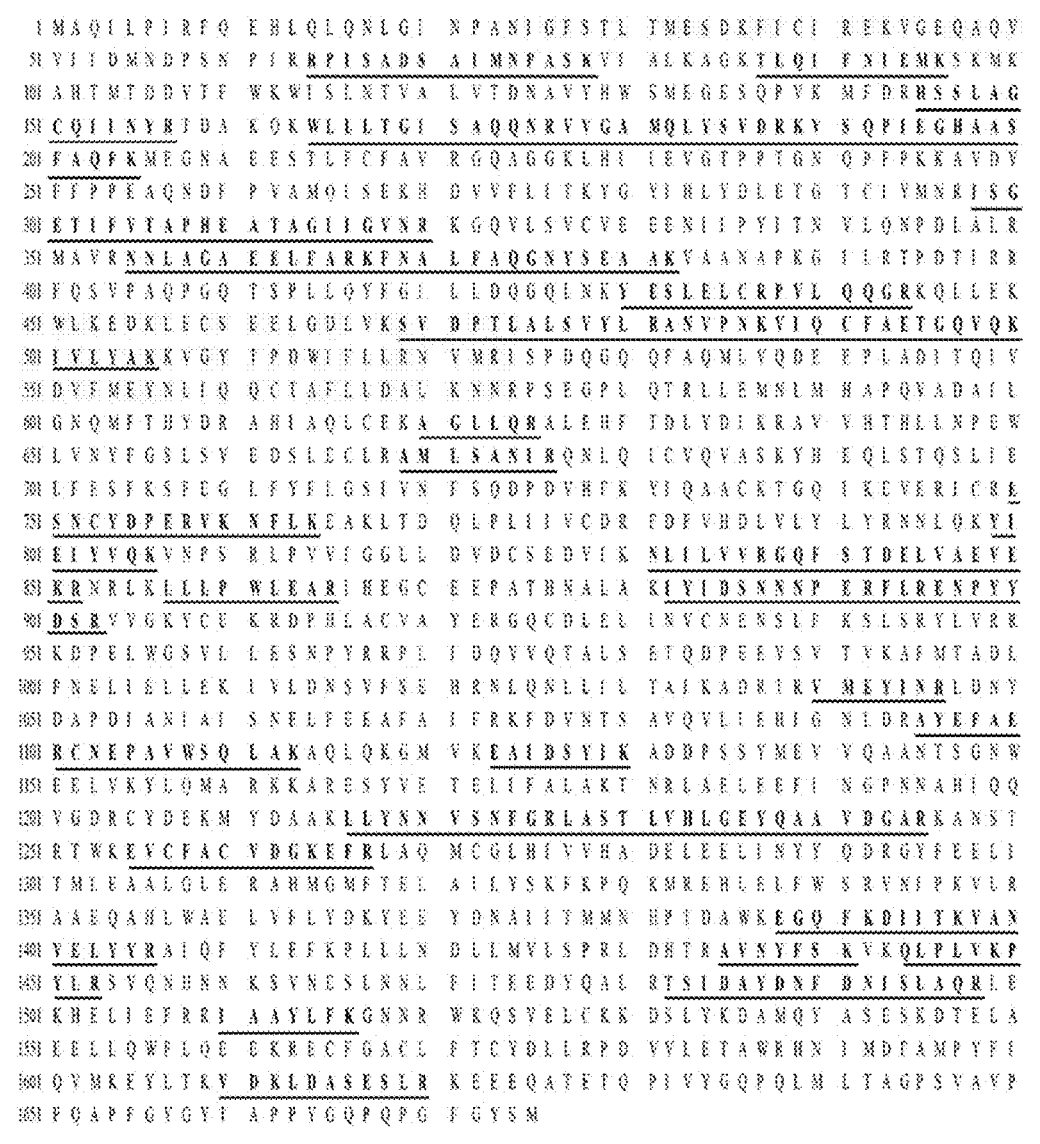

To identify the target of Pa65-2, MIA PaCa-2 total cell lysates were prepared and purified by Pa65-2-conjugated immunoaffinity chromatography. Silver stain and Western blotting demonstrated that Pa65-2 recognized a target protein with a molecular weight of 190 kDa (FIG. 1D). According to LC-MS/MS analysis and Swiss-Prot database searching, the target protein of Pa65-2 is human clathrin heavy chain (CHC) (FIG. 10). The specificity of Pa65-2 to CHC was confirmed by conducting immunoprecipitation and Western blot analysis in parallel using a commercial CHC antibody, mAb X-22, whose CDR is unknown (FIG. 1E). Western blot analysis using Pa65-2 showed a dramatic decrease in signal after CHC knockdown (FIG. 2A). These data further confirmed that Pa65-2 specifically recognized CHC. Three complementarity-determining regions (CDRs) in the heavy and light chains of Pa65-2 are shown in Table 1.

Suppressing CHC Expression Inhibits Pancreatic Cancer Growth

To evaluate the functional role of CHC in tumorigenesis, CHC expression was knocked down by shRNA in MIA PaCa-2 cells. When CHC were knockdown in MIA PaCa-2 cells (FIG. 2A), the growth rate (FIG. 2B), colony formation (FIG. 2C) and invasion ability (FIG. 2D) of the cancer cells were significantly reduced. However, suppression of CHC expression in human skin fibroblast had no effect on the proliferation rate of the cells (FIG. 11). To examine the effect of down-regulating CHC expression on tumor growth in vivo, a xenograft model was generated by injecting MIA PaCa-2 cells with CHC gene knockdown on one side of the NOD/SCID mouse, and control on the other side. We found that knockdown of CHC markedly reduced xenograft tumor growth (FIG. 2E-G). On average, the suppression of CHC resulted in a 92.6% reduction in tumor growth compared with the controls at day 45 (FIG. 2E). On day 50, mice were sacrificed and tumors were dissected. (FIG. 2F) to measure the tumor weight (FIG. 2G). While one mouse showed no tumor on the CHC knockdown side, the other seven mice showed tumors with miniscule sizes on their CHC knockdown sides (FIG. 2F). The same results were observed in CHC knockdown CL1-5 lung cancer cells (FIGS. 12A-E). Furthermore, TUNEL staining showed that CHC knockdown increased apoptosis of the tumor cells (FIG. 2H). These results indicate that CMC may play a role in the regulation of tumorigenesis.

CHC Regulates VEGF Expression in Pancreatic Cancer

Figure 13:
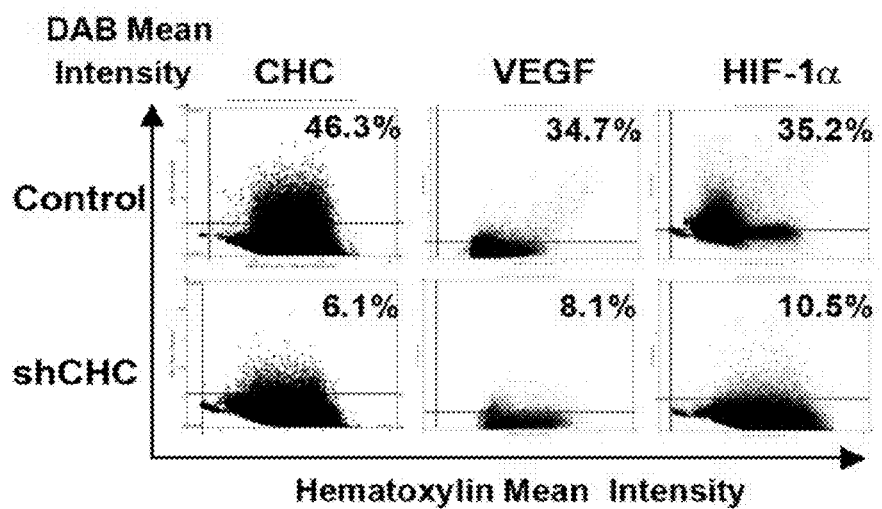
FIG. 13 shows quantification of CHC, VEGF and HIF-1α staining was performed on consecutive sections using Histo-Quest analysis software.

Knockdown of CHC markedly reduced tumor growth (FIGS. 2E-G). To investigate whether loss of CHC expression could inhibit tumor angiogenesis, immunofluorescent staining with CD31 was performed. Knockdown of CHC resulted in a 78% reduction in tumor blood vessels in mouse xenografts (FIG. 3A). Since it is well known that HIF-1α-mediated VEGF axis plays an important role in tumor angiogenesis, we further investigated whether knockdown of CHC had an impact on HIF-1α and VEGF expressions. Results showed that the protein expression, levels of CHC, VEGF, and HIF-1α in the tumor xenografts were significantly reduced in the CHC knockdown group (FIG. 3B and FIG. 13), in addition, mRNA level of CHC and VEGF were lowered in CHC knockdown tumor tissues, compared to the control tumor tissues (FIG. 3C). However, the decreased expression of HIF-1α in CHC knockdown xenograft tumor was observed only in protein level (FIG. 3B and FIG. 13) but not in the mRNA level (FIG. 3C), Upon further evaluation of CHC and VEGF mRNA levels in nineteen human pancreatic cancer panels, we found a correlation between the expressions of CHC and VEGF (coefficiency =0.299; minor correlation, P=0.02) (FIG. 3D).

We further investigated the molecular mechanism of CHC on the regulation of VEGF gene expression. VEGF mRNA was increased in mock cells under hypoxia treatment, whereas it was decreased markedly under both hypoxic and normoxic conditions when CHC was knocked down (FIG. 3E). Luciferase assay also showed that CHC can participate in the regulation of VEGF-A promoter activity (FIG. 3F). To directly determine whether CHC binds to the hypoxia-response element (HRE) of VEGF-A promoter, we performed chromatin immunoprecipitation (ChIP) assays in CHC-expressing and knockdown cells. It was found that CHC bound to the VEGF-A promoter region (FIG. 3G) and that there was a significant decrease in the binding of CHC and HIF-1α to the VEGF-A promoter region in CHC knockdown cells (FIG. 3G-H). These observations suggest that CHC may interact with HIF-1α and co-localize onto the HRE of the VEGF-A promoter, which can then induce VEGF-A expression.

CHC Interacts with and Stabilizes HIF-1α in MIA PaCa-2 Cells

Figure 4:
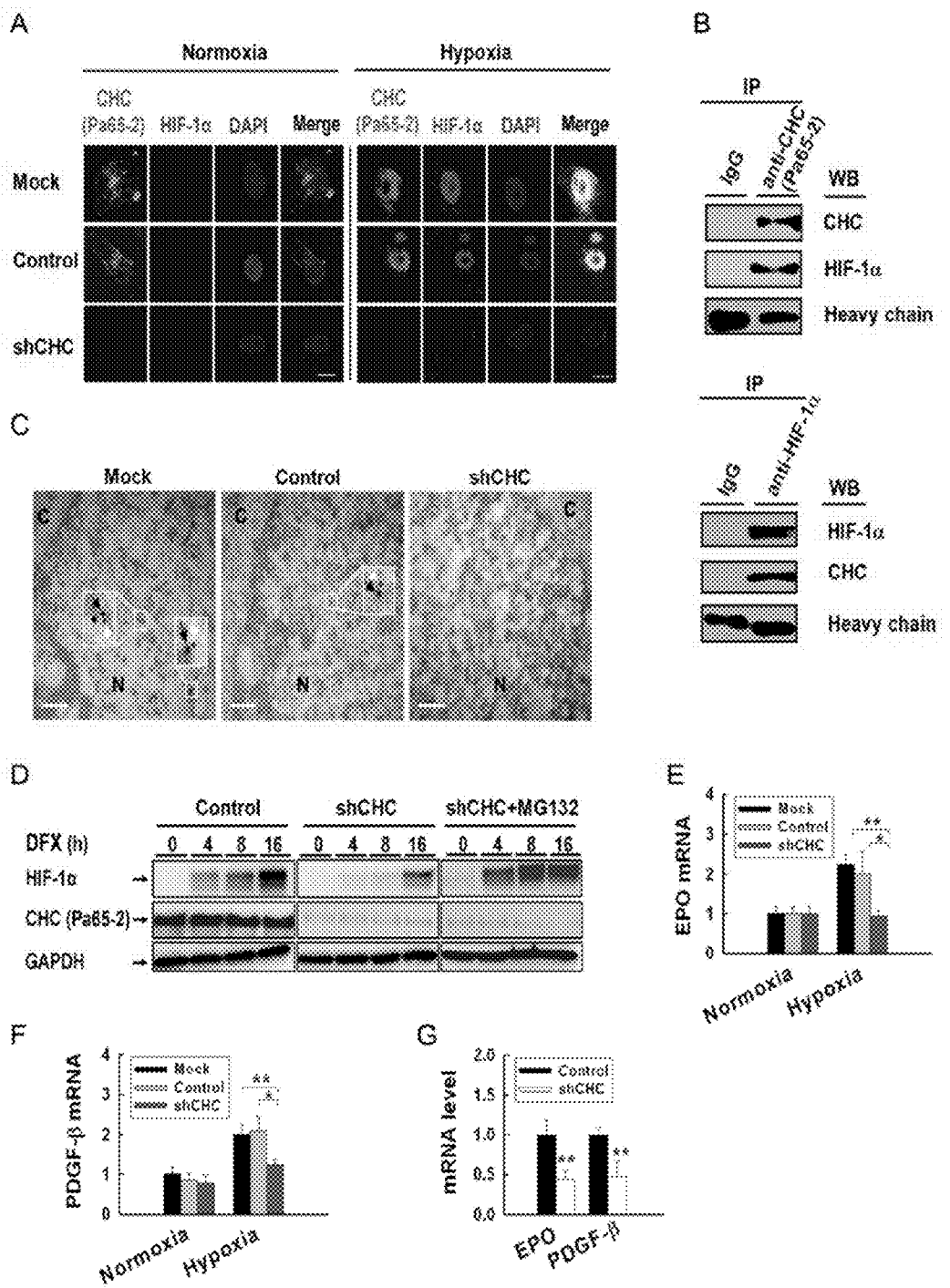
FIG. 4 shows CHC interacts with and stabilizes HIF-1α in MIA PaCa-2 cells. (A) Co-localization of CHC and HIF-1α after double immunofluorescent staining with antibodies against CHC (FITC staining would show green color) or HIF-1α (Rhodamine staining would show red color) was analyzed by confocal microscopy. Scale bar, 10 µm, (B) Co-immunoprecipitation of cell lysates with antibodies against CHC and HIF-1α and subsequent immunoblotting with Pa65-2 and anti-HIF-1α antibodies. (C) Co-localization of CHC and HIF-1α in the nuclei of MIA PaCa-2 cells by double labeling immuno-electron microscopy. Mock (left panel) and control (middle panel) cells both showed co-localization of CHC, labeled by 18 nm colloidal gold conjugated antibody (arrows, insert), and HIF-1α, labeled by 12 am colloidal gold conjugated antibody (white arrows, insert), in the nuclear regions, N. shCHC-transduced cells (right panel) showed marked reduction of CHC signaling and negligible labeling of HIF-1α in the nucleus (C, cytosol, N, nucleus). Scale bar, 200 nm. (D) MIA PaCa-2 cells were incubated with DFX (100 µM) for 0 to 16 h in the absence (left, and middle panel) or presence of the proteasome inhibitor MG-132 (10 µM) (right panel). Whole-cell lysates from different time intervals were analyzed by Western blot analysis. (E) Quantitative RT-PCR analyses of EPO and (F) PDGF-β mRNA in CHC knockdown MIA PaCa-2 cells. Error bars denote ±SD. *P<0.05; P<0.01. (G) Quantitative RT-PCR analyses of EPO and PDGF-p gene expressions in xenograft tumors. Gene expression levels were normalized to GAPDH signal Error bars denote ±SD. P<0.01.
Figure 12:
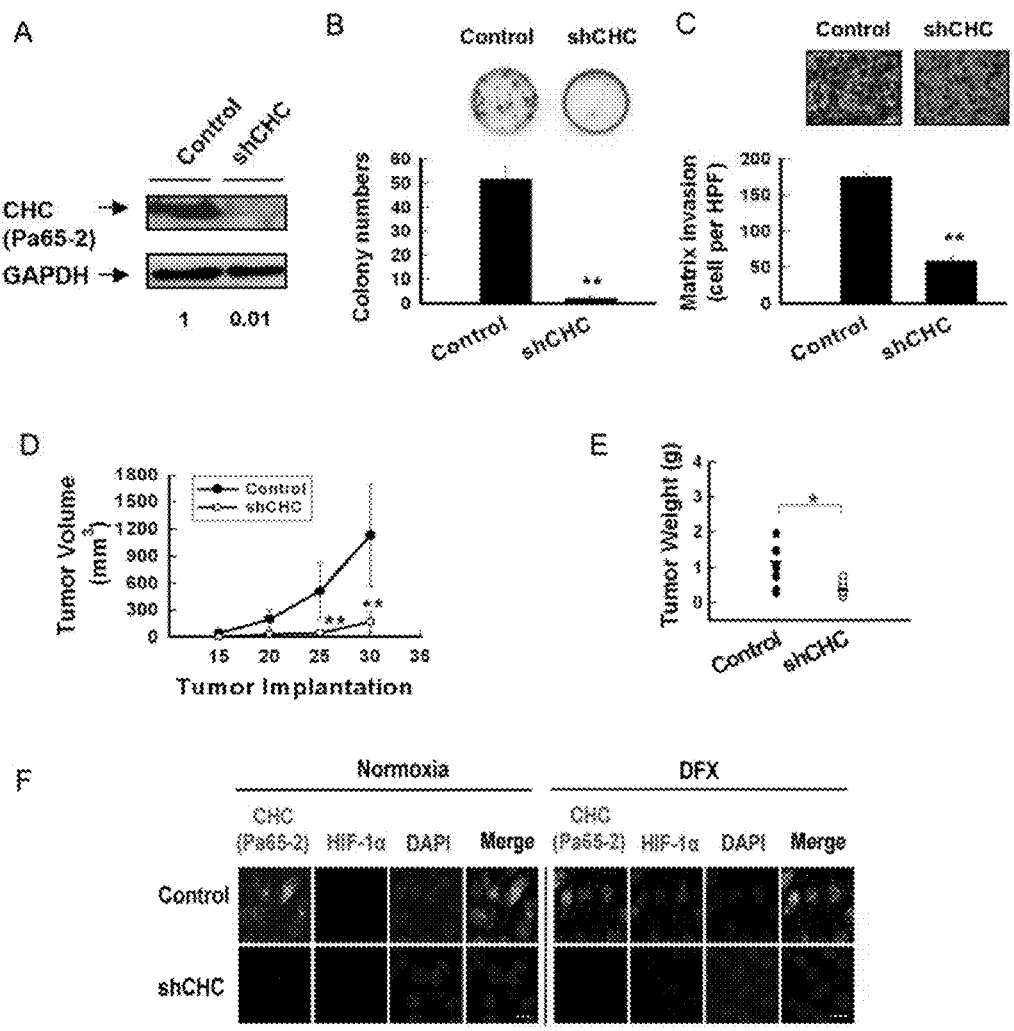
FIG. 12 shows suppression of CHC expression inhibits lung cancer cells growth and invasion. (A) CHC knockdown was determined by Western blot. (B) Knockdown of CHC expression reduced colony formation potential of CLI-5 cells. Error bars denote ±SD. P<0.01. (C) Knockdown of CHC expression reduced cell invasion. Scale bar, 40 µm; Error bars denote ±SD. P<0.01. (D) Eight NOD/SCID mice were injected s.c, ($1\times10^7$ cells) in the lateral portion of the hind limb, left side for the control vector-transduced CLI-5 cells, and right side for the CHC shRNA-transduced CLI-5 cells. The tumors were measured with calipers every five days, and tumor volume was calculated as length x (width)$^2$×0.52. Error bars denote ±SD. **P<0.01. (E) Tumor weight was measured. Error bars denote ±SD. *P<0.05. (F) Colocalization of CHC and HIF-1α, shown by immunofluorescence, in CL1-5 cells incubated with DFX (100 µM) for 5 h (right, panel) or with 20% $O_2$ for 5 h (left panel). Scale bar, 10 µm.

To investigate whether CHC could interact with HIF-1α, we assessed the co-localization of CHC and HIF-1α by confocal microscopy. Interestingly, CHC was found in 80% of the nuclei of the MIA PaCa-2 cells, while HIF-1α was found in 83% of nuclei of MIA PaCa-2 cells during hypoxia. Together, 70% the nuclei of the MIA PaCa-2 cells contained both CHC and HIF-1α during hypoxia (FIG. 4A and FIGS. 14A-C). However, when CHC was knocked down, a low level of HIF-1α was detected, in either cytoplasm or nuclei (FIG. 4A and FIGS. 14A-C). The same results were observed in CL1-5 lung cancer cells (FIG. 12F). Subsequently, immunoprecipitation and immuno-electron microscopy were applied to verify protein interaction between CHC and HIF-1α. As shown in FIG. 4B, HIF-1α and CHC were co-immunoprecipitated with each other. The double labeling immuno-electron microscopy data further showed that CHC and HIF-1α were present in the nuclei as well as in the cytoplasm of MIA PaCa-2 cells. The co-localization of CHC and HIF-1α was particularly noticeable inside the nuclei in both mock and control cells (FIG. 4C), suggesting an interaction between, the two proteins.

Figure 14:
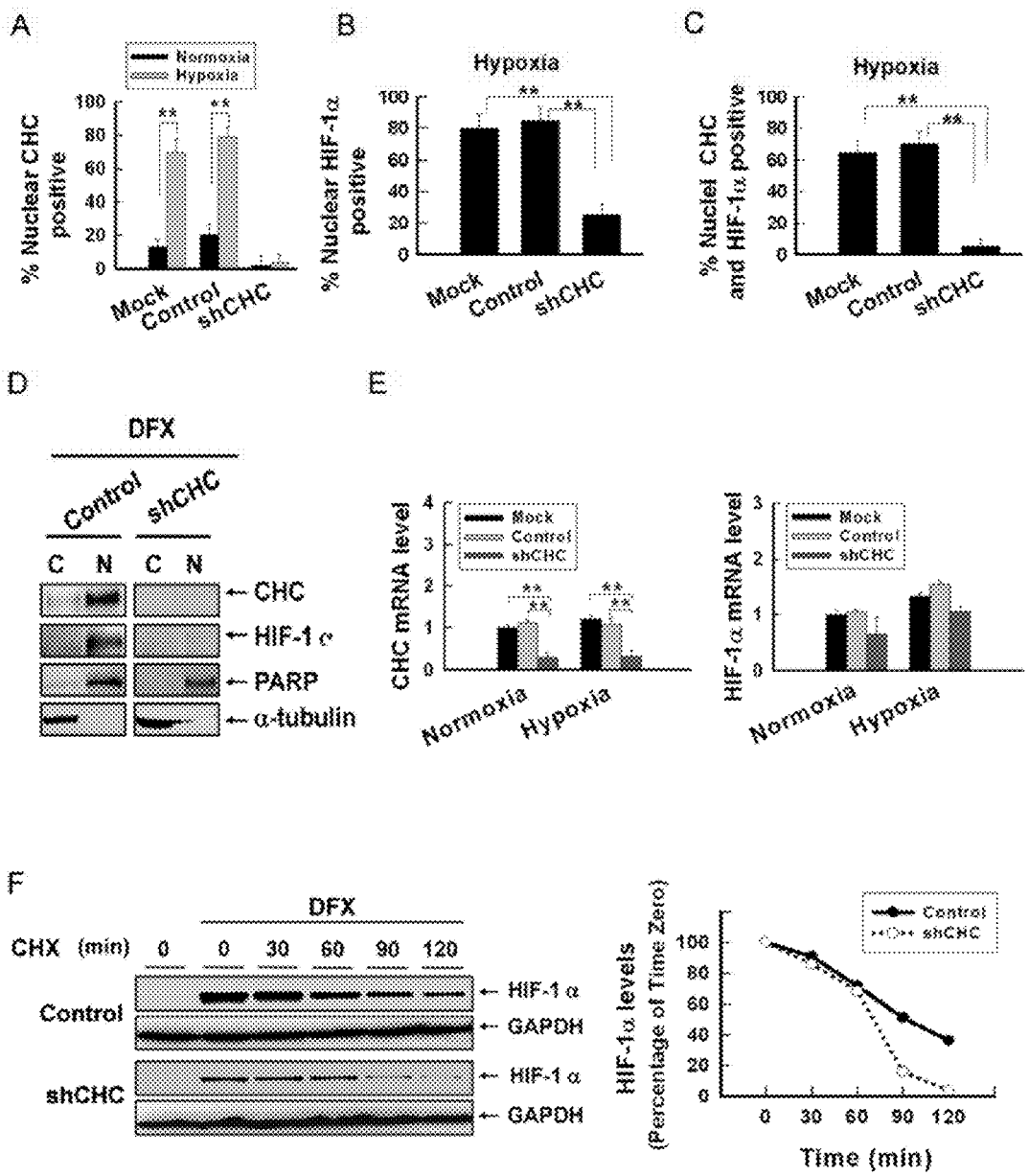
FIG. 14 shows CHC knockdown facilitated HIF-1α protein degradation in MIA PaCa cells. The percentage of (A) CHC, (B) HIF-1α, (C) HIF-1α and CHC positive nuclei is shown in FIG. 4A. Three independent fields of 1 mm$^2$ each were counted. The application of the quantitative methods described previously (3), Error bars denote ±SD. P<0.01. (D) Immunoblot analysis of cytoplasmic, C, and nuclear, N, fraction of MIA PaCa-2 cells treated with DFX (100 µM) for 16 h (anti-PRAP-1 and anti-α-tubulin serving as internal control), (E) Quantitative RT-PCR analysis of CMC (left panel) and HIF-1α (right panel) mRNA in CHC knockdown MIA PaCa-2 cells cultured in normoxic or hypoxic conditions. Gene expression levels were normalized to GAPDH signal. Error bars denote ±SD. P<0.01. (F) MIA PaCa cells were first incubated in the presence of DFX (100 µM) for 16 h and then treated, with CHX (5 µg/ml) in control and shCHC cells for indicated times. Cells were harvested and whole-cell lysates analyzed for HIF-1α protein level by immunoblotting (left panel). The band intensity, as determined by densitometry, was normalized to the GADPH signal and expressed as percent of the HIF-1α abundance at time zero (right panel).

It was noticed that the protein level of HIF-1α, which was induced by hypoxia, was decreased in CHC knockdown cells (FIG. 4C and FIG. 14D), whereas the mRNA level of HIF-1α was not affected by CHC knockdown (FIG. 14E), suggesting that CHC may influence HIF-1α protein stability. To test whether knockdown of CHC decreased the stability of HIF-1α protein, cells were treated with cycloheximide (CHX) to block de novo protein synthesis. The results suggested that suppression of CHC decreased HIF-1α protein stability (FIG. 14F). However, the decreased protein level of HIF-1α in CHC knockdown, cells was rescued with the presence of MG132 (a proteosome inhibitor) (FIG. 4D). We further analyzed the expressions of HIF-1α-dependent genes in CHC knockdown cells. The results showed that knockdown of CHC inhibited EPO (FIG. 4E) and PDGF-β gene expressions (FIG. 4F). Similar data were also obtained in tumor xenograft (FIG. 4G). Together, these data suggest that the interaction between CHC and HIF-1α may protect HIF-1α protein stability.

Inhibition of Ligand Internalization and Cell Growth by Pa65-2

Figure 5:
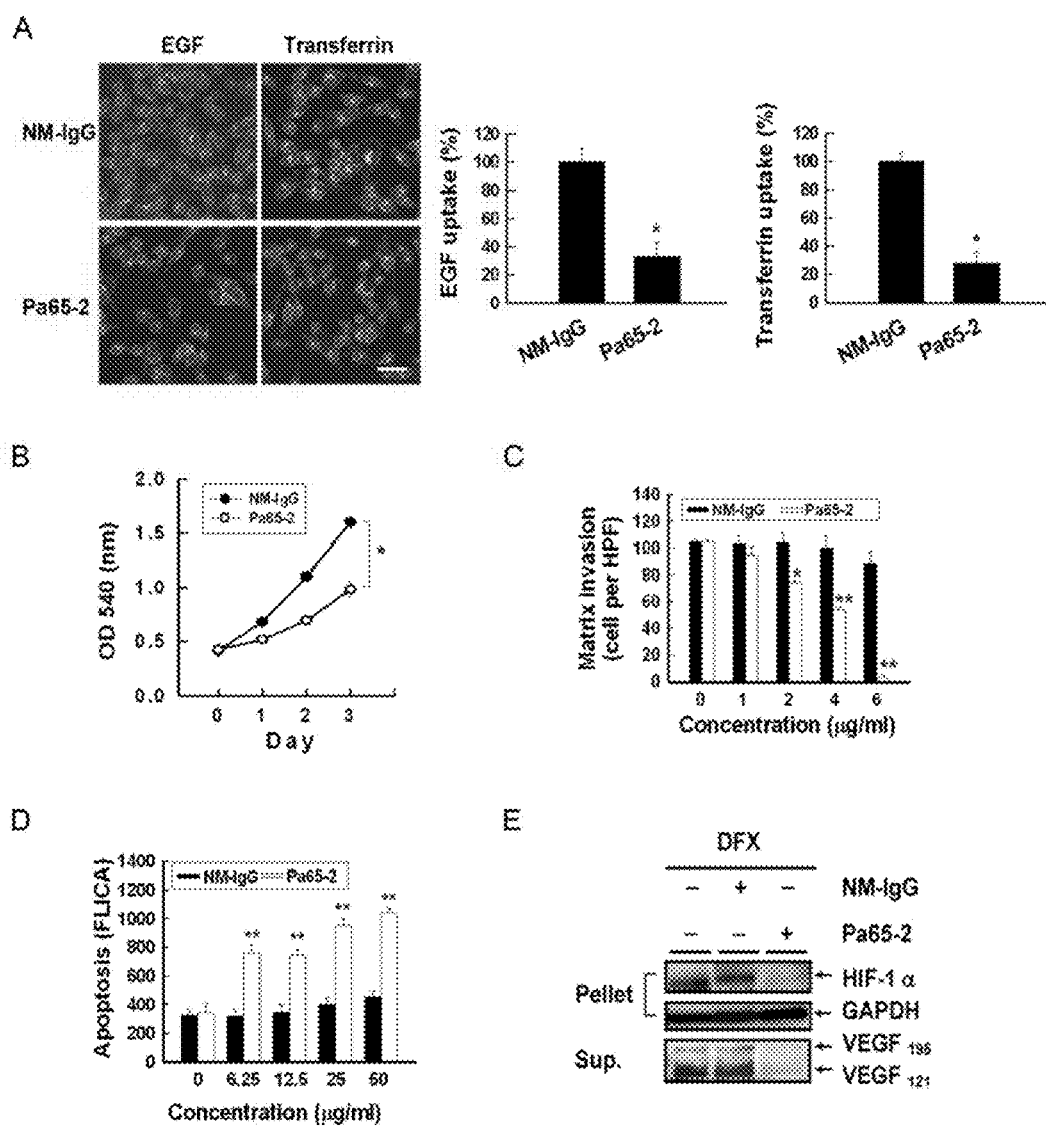
FIG. 5 shows inhibition of ligand internalization and pancreatic cancer cells growth by Pa65-2. (A) Immunofluorescent analysis of EGF and transferrin internalization in MIA PaCa-2 cells after CHC inhibition by Pa65-2. MIA PaCa-2 cells, which were pretreated with Pa65-2 or NM-IgG at 37° C. and subsequently incubated with Alex 555-EGF (1 µg/ml) or Alex 555-transferrin (50 µg/ml) at 37° C. (red: Rhodamine staining), were subjected to plasma membrane staining using WGA-Alex 647 (green) and nucleus staining using DAPI (blue). Scale bar, 20 µm. (left, panel). The percentage of EGF-Alex 555 (middle panel) or transferrin-Alex 555 (right panel) staining was calculated based on a total of 100 MIA PaCa-2 cells. Staining was analyzed by confocal. microscopy. Error bars denote ±SD. *P<0.05. (B) MIA PaCa-2 cells were treated with Pa65-2 or NM-IgG (50 µg/ml) for 3 days. Cell proliferation was detected by MTT (3-(4,5-cimetlrylthi-azol-2-yl)-2,5-diphenyl tetrazolium bromide) analysis. Error bars denote cfc SD. *P<0.05. (C) Pa65-2 inhibited MIA PaCa-2 cell invasion. Error bars denote ±SD. *P<0.05; P<0.01. (D) Pa65-2 induced MIA PaCa-2 cell apoptosis. Error ban denote ±SD. P<0.01. (E) MIA PaCa-2 cells were incubated with DFX (100 µM) in the presence of Pa65-2 (50 µg/ml) or NM-IgG (50 µg/ml) for 48 h. The culture media and whole-cell lysates were analyzed by Western blot analysis.

Clathrin-mediated endocytosis (CME) is a major mechanism for the internalizations of plasma-membrane receptors. We evaluated the effect of Pa65-2 on the internalization of epidermal growth factor (EGF) and transferrin (Tf), known ligands for CME (30,31). As shown in FIG. 5A, treatment with Pa65-2 blocked EGF and transferrin uptake in MIA PaCa-2 cells. In addition, treatment of Pa65-2 not only inhibited cancer cell proliferation (FIG. 5B) and migration (FIG. 5C), but it also induced cell apoptosis in MIA PaCa-2 cells (FIG. 5D). Western blot analysis showed that treatment with Pa65-2 suppressed hypoxia-induced HIF-1α expression and VEGF secretion (FIG. 5E). However, treatment with normal mouse IgG (NM-IgG) showed no inhibitory activities (FIGS. 5A-E). Moreover, it was also found that Pa65-2 suppressed VEGF internalization and induced apoptosis in HUVECs (FIG. 15).

Pa65-2 Suppression of Pancreatic Xenograft Tumor Growth

Figure 6:
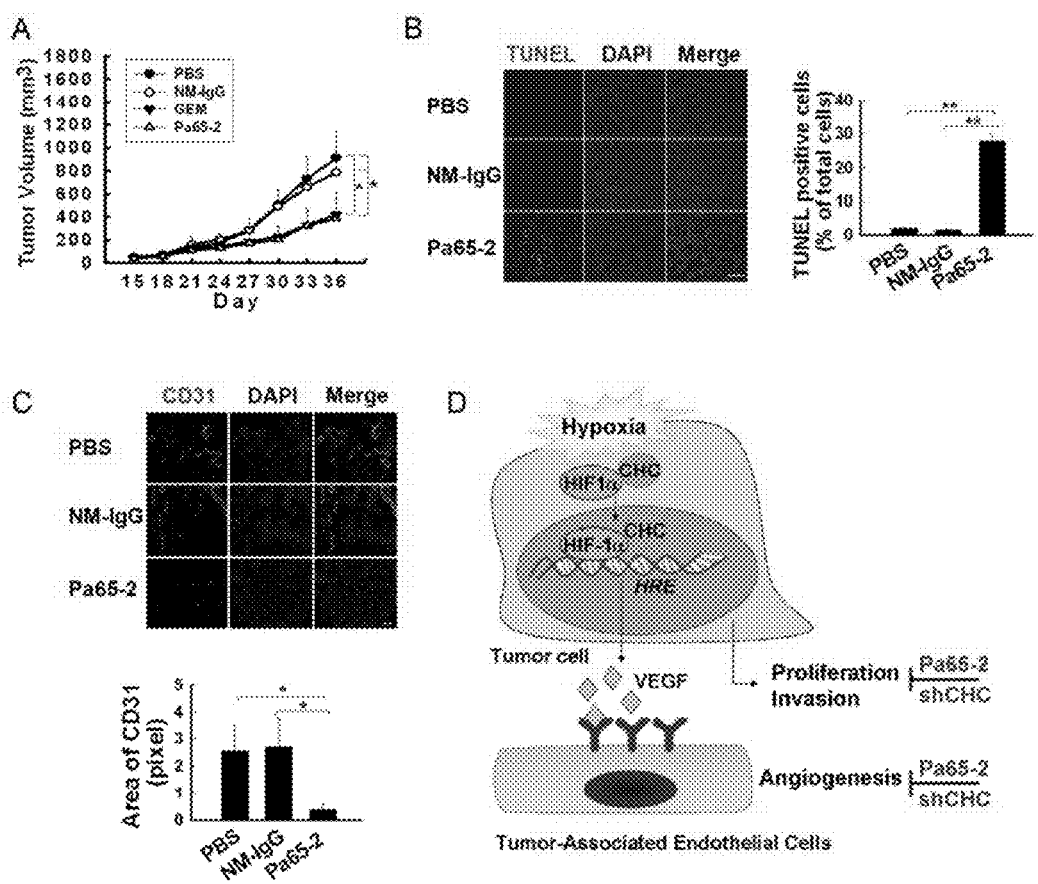
FIG. 6 shows Pa65-2 suppression of pancreatic xenograft tumor growth. (A) Tumor-bearing mice (average tumor sizes ranging from 40 to 60 mm³), received i.v. injections with 10 mg/kg of Pa65-2 or 15 mg/kg of gemcitabine (GEM), or NM-IgG, or PBS. Tumor sizes were measured every three days (n=6, each group). Error bars denote ±SD. *P<0.05. (B) Detection of Pa65-2 -induced apoptosis in tumor tissues by TUNEL staining (left panel). Quantification of fluorescence intensity was performed using MetaMorph software (right panel). Scale bar, 200 µm; Error bars denote ±SD. **P<0.01. (C) Expression of endothelial marker (CD31) within tumor sections was analyzed by immunofluorescent staining (upper panel). Quantification of fluorescence intensity was performed using MetaMorph. software (lower panel). Scale bar, 200 µm; Error bars denote ±SD. *P<0.05. (D) Schematic representation of the proposed mechanism of CMC mediation of tumors genesis. Under hypoxic conditions, CHC has an additional role of mediating hypoxia-induced angiogenesis. CHC interacts with and stabilizes HIF-1α. CHC plays an assisting role in HIF-1α nuclear localization and HRE promoter binding, which lead to an increased production of VEGF. Suppression of CHC expression can inhibit tumorigenesis and angiogenesis.
Figure 16:
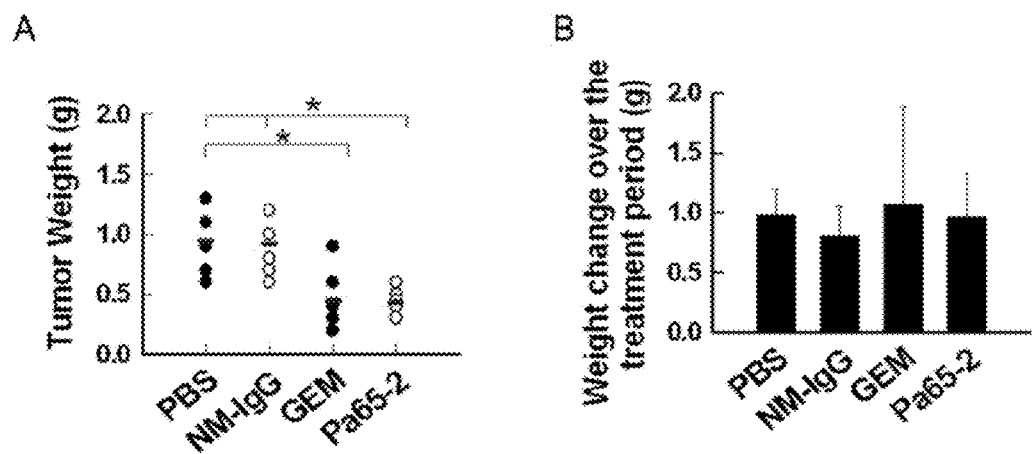
FIG. 16 shows the results of comparing antitumor efficacy of Pa65-2 and GEM in NOD/SCID bearing human pancreatic cancer xenografts. (A) Tumor weight was measured. Error bars denote ±SD. *P<0.05. (B) Different treatments have no effects on body weight change (n=6 in each group).

Since CHC shRNA knockdown severely affected xenograft tumor growth in vivo, we investigated whether Pa65-2 could be used to directly inhibit tumor angiogenesis and growth in pancreatic cancer, NOD/SCID mice were inoculated with MIA PaCa-2 cells. When the tumors grew up to 50 mm$^3$, mice were administrated with Pa65-2 (10 mg/kg), NM-IgG, or PBS every three days. Results showed that in the Pa65-2-treated groups, the average tumor volume were about 2 fold smaller than the control groups at day 36 (n=6, P<0.05; FIG. 6A and FIG. 16A). When analyzing the tumor sections, it was found that the apoptotic cells were increased (n=6, P<0.01; FIG. 6B) while the blood vessels were decreased (P<0.05; FIG. 6C) in Pa65-2-treated tumors. We further compared the inhibitory effect of Pa65-2 and gemcitabine, a widely accepted first-line treatment for pancreatic cancer, on tumor growth. Results showed that treatment with Pa65-2 had equivalent effects as treatment with gemcitabine (FIGS. 6A and 16B). These findings show that Pa65-2 possesses the ability to inhibit pancreatic tumor growth and angiogenesis.

TABLE 1

V$_H$ domains (SEQ ID NO: 2)

| FW1 | CDR1 | FW2 | CDR2 |
|---|---|---|---|
| EVKLVESGGGLVKPGG SLNISCAASGETES (SEQ ID NO: 10) | NYVMS (SEQ ID NO: 4) | WVRQTPEKRLEW VA (SEQ ID NO: 11) | TISSGDNYMYYPDS VKG (SEQ. ID NO: 5) |

| FW3 | CDR3 | FW4 | |
|---|---|---|---|
| RFTISSDNAKNTLFLQM SSLRSEDTALNYCAR (SEQ ID NO: 12) | HFDNYEGNSMDY (SEQ ID NO: 6) | WGQGTSVTVSSA KTTPPSDYPLA (SEQ. ID NO: 13) | |

V$_L$ domains (SEQ ID NO: 3)

| FW1 | CDR1 | FW2 | CDR2 |
|---|---|---|---|
| DIVLTQSPATLSVTPGD SVSLSC (SEQ ID NO: 14) | RASQSIRSNLH (SEQ ID NO: 7) | WYQQKSHESPRL LIK (SEQ ID NO: 15) | YASQSIS (SEQ ID NO: 8) |

| FW3 | CDR3 | FW4 | |
|---|---|---|---|
| GIPSRFSGSGSGTDFILSI NSVATEDECNYFC (SEQ ID NO: 16) | QQSNSWPL (SEQ ID NO: 9) | TFGAGTKLELKR ADAAPTVS (SEQ ID NO: 17) | |

Complementarity-determining regions 1-3 (CDR1-3), and framework regions 1-4 (FW1-4) for both the V$_H$ and V$_L$ domains are shown. The V domain families were aligned by igblast database.

Table 1 shows the amino acid sequences of V$_H$ and V$_L$ domains of anti-CMC monoclonal antibody, which is related to the SEQ ID NO: 1 shown in FIG. 10.

Table 2 shows CHC expression in human pancreas cancer tissue arrays. We modified the "Quick Score" methods by reducing the original scales (Siegel et al. (2012) "Cancer statistics 2012" *CA Cancer J Clin*, 62, 10-29). Two indices were used in evaluating the staining results of tumors. Labeling Index (LI) indicates the number of tumor cells that were immunostained (or "positive cells") as a proportion of the overall number of cells. A score on a scale of 0-2 was assigned; 0-10%=0, 11-49%=1, 50-100% =2. The second index is the Intensity Index (II), which measures the average intensity of the immunostaining. A score on a scale of 0-2 was assigned; no staining=0, weak staining=1, and strong staining=2. The scores from these two indices were added to give the tumor Labeling Score (LS), which ranges from 0-4.

TABLE 2

| Pancreas Cancer | Stage | Labeling Score |
|---|---|---|
| Normal Pancreas | | 0 |
| Adenocarcinoma I | T2N0M0 | 3 |
| | T2N1M0 | 2 |
| | T3N0M0 | 3 |
| | T3N1M0 | 3 |
| Adenocarcinoma II | T2N0M0 | 2 |
| | T3N0M0 | 3 |
| | T3N1MX | 3 |
| | T4N1M1 | 4 |
| Adenocarcinoma III | T3N0M0 | 3 |
| | T3N1MX | 3 |

Table 3 shows the list of primers for cloning. Table 4 shows the list of primers for Quantitative RT-PCR. Table 5 shows list of primers for ChIP, Table 6 shows the list of primers for cDNA synthesis and amplification of variable region.

TABLE 3

| Name | Sequence (5'-3') |
|---|---|
| VEGF f | GGTACCGGGCCACGGAGTGACTGGTGAT (SEQ ID NO: 18) |
| VEGF r | CTCGAGGGAAGAGAGAGACGGGGTCAGAGAGA SEQ ID NO: 19) |

TABLE 4

| Name | Sequence (5'-3') |
|---|---|
| CLTC f | GACAAAGGTGGATAAATTAGATGC (SEQ ID NO: 20) |
| CLTC r | TAAACAATGGGTTGTGTCTCTGTA (SEQ ID NO: 21) |
| VEGF f | ACATCTTCCAGGAGTACCC (SEQ ID NO: 22) |
| YEGf r | CTTGGTGAGGTTTGATCCG (SEQ ID NO: 23) |
| HIF-1α f | GGTTCACTTTTTCAAGCAGTAGG (SEQ ID NO: 24) |
| HIF-1α r | GTGGTAATCCACTTTCATCCATT (SEQ ID NO: 25) |
| EPO f | AGCAGGAAGCATTCAGAGA (SEQ ID NO: 26) |
| EPO r | AGGTAAATCGCCTCCAAAG (SEQ ID NO: 27) |
| PDGF-β f | CTGGCATGCAAGTGTGAGAC (SEQ ID NO: 28) |
| PDGF-β r | CGAATGGTCACCCGAGTTT (SEQ ID NO: 29) |
| GAPDH f | CTTCACCACCATGGAGGAGGC (SEQ ID NO: 30) |
| GAPDH r | GGCATGGACTGTGGTCATGAG (SEQ ID NO: 31) |

TABLE 5

| Name | Sequence (5'-3') |
|---|---|
| VEGF f | GAGCCCGCGCCCGGAGG (SEQ ID NO: 32) |
| VEGF r | CAGCCCAGAAGTTGGAC (SEQ ID NO: 33) |
| GAPDH f | AGGTGAAGGTCGGAGTCAAC (SEQ ID NO: 34) |
| GAPDH r | TCTTCTGGGTGGCAGTGATG (SEQ ID NO: 35) |

TABLE 6

| Name | Sequence (5'-3') |
|---|---|
| VH1FOR | d(TGAGGAGACGGTGACCGTGGTCCCTTGGCCCCAG) (SEQ ID NO: 36) |
| VK1FOR | d(GTTAGATCTCCAGCTTGGTCCC) (SEQ ID NO: 37) |
| VH1BACK | d(AGGTSMARCTGCAGSAGTCWGG-3* (in which S = C or G, M = A or C, R = A or G, and W = A or T) (SEQ ID NO: 38) |
| VK1RACK | d(GACATTCAGCTGACCCAGTCTCCA) (SEQ ID NO: 39) |

Table 6 shows the list of primers for cDNA synthesis and amplification of the variable region of IgG, As shown in Table 6, the primer VH1BACK includes $2^5$ different sequences. The sequence AGGTCAAACTCCAGSAGTCAGG (SEQ ID NO: 38) is a representative sequence of them.

Discussion

Pa65-2, generated by screening hybridomas against MIA PaCa-2, was found to specifically bind to the cell surface and cytosol of various cancer and tumor blood vessels through interaction with its target, CHC. This study demonstrated that CHC expression is upregulated in cancer cells as well as in tumor-associated endothelial cells. We found that inhibition of CHC by Pa65-2 or shRNA could inhibit tumor growth and angiogenesis. Chip assays indicated that CHC interacted with HIF-1α and participated in the regulation of VEGF transcription. Knockdown of CHC expression also decreased the protein stability of HIF-1α. To our knowledge, this is the first study to demonstrate that CHC promotes angiogenesis and tumor growth by stabilizing HIF-1α, followed by upregulating the expression of VEGF.

Our current study found higher expression levels of CHC in pancreatic cancer tissues as well as in other cancer types. In addition, we found that Pa65-2 binds to tumor cells as well as to tumor-associated endothelial cells. These finding suggest that the expression of CHC in tumor and tumor-associated endothelial cells may be responsible for increasing uptake of growth factors by endocytosis under pathological conditions. Diminishing CHC levels by shRNA resulted in decreased protein stability of HIF-1α and decreased expressions of HIF-1α down-stream genes.

Base on the studies, it was proposed that the CHC promotes tumor growth and angiogenic process through two pathways. One is to increase the uptake of growth factors or receptors by clathrin-mediated endocytosis; the other is to increase the expression of VEGF, possibly by interacting and stabilizing HIF-1α under hypoxic condition (FIG. 6D). In conclusion, we have generated a monoclonal antibody, Pa65-2, which specifically binds to pancreatic cancer cells and tumor-associated endothelial cells through its recognition of CHC. Our results strongly implicate CHC in promoting tumor growth, invasion and angiogenesis in vitro and in vivo, Pa65-2 inhibited EGF, Tf and VEGF internalizations, and had similar anti-tumor activity as gemcitabine. Our results suggest that Pa65-2 mAb or CHC shRNA can potentially be used to reduce cancer cell invasion, migration and VEGF expression, and to inhibit tumor growth and angiogenesis.

In summary, Pancreatic adenocarcinoma is an aggressive disease with a high mortality rate. Currently, treatment options are limited. In an effort to improve the efficacy of treatments for pancreatic adenocarcinoma, we have generated a monoclonal antibody (mAb), Pa65-2, which specifically binds to pancreatic cancer cells and tumor blood vessels but not to normal cells. The target protein of Pa65-2 is identified as human clathrin heavy chain (CHC; SEQ ID NO: 1). We found that knockdown of CHC or Pa65-2 treatment not only reduced cancer cell proliferation, colony formation and invasion, but it also induced cancer cell apoptosis. In vivo study showed that suppression of CHC either by shRNA or by Pa65-2 inhibited tumor growth and angiogenesis. One of the key functions of CHC was to bind with the hypoxia-inducing factor (HIF)-1α protein, increasing the stability of this protein and facilitating its nuclear translocation and hypoxia responsive element (HRE) promoter binding, thereby regulating the expression of vascular endothelial growth factor (VEGF). Knockdown of CHC results in downregulations of both HIF-1α and its downstream target gene expressions, such as VEGF, erythropoietin (EPO) and platelet-derived growth factor-β (PDGF-β). Pa65-2 treatment blocked cancer cells' uptake of epidermal growth factor (EGF) and transferrin (Tf), inhibited cancer cell proliferation, invasion, and induced cancer cell apoptosis. Taken together, our findings indicate that CHC plays a role in the processes of tumorigenesis and angiogenesis. Pa65-2 antibody or CHC shRNA can potentially be used for pancreatic cancer therapy.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A purified monoclonal antibody or an antigen-binding fragment thereof which specifically binds to human clathrin heavy chain (CHC) comprising the amino acid sequence of SEQ ID NO: 1 and comprises a heavy chain variable region comprising the amino acid sequence of SEQ ID NO: 2.

2. The purified monoclonal antibody or antigen-binding fragment thereof of claim 1,
wherein the purified monoclonal antibody comprises a light chain variable region comprising the amino acid sequence of SEQ ID NO: 3.

3. The purified monoclonal antibody or antigen-binding fragment thereof of claim 1, which binds to cells selected from the group consisting of pancreatic cancer cells, breast cancer cells, lung cancer cells, ovary cancer cells, oral cancer cells, and tumor-associated endothelial cells.

4. An isolated monoclonal antibody or an antigen binding fragment thereof binging to human clathrin heavy chain (CHC) and comprising:
(a) a heavy chain variable region, comprising:
(i) complementarity determining region 1 (CDR1) comprising SEQ ID NO: 4;
(ii) complementarity determining region 2 (CDR2) comprising SEQ ID NO: 5; and
(iii) complementarity determining region 3 (CDR3) comprising SEQ ID NO: 6; and
(b) a light chain variable region, comprising.
(i) CDR1 comprising SEQ ID NO: 7;
(ii) CDR2 comprising SEQ ID :NO: 8; and
(iii) CDR3 comprising SEQ ID NO: 9.

5. The isolated antibody or binding fragment of claim 4, wherein the binding fragment comprises an Fv fragment of the antibody.

6. The isolated antibody or binding fragment of claim 4, wherein the binding fragment comprises an Fab fragment of the antibody.

7. The isolated antibody or binding fragment of claim 4, wherein the antibody is a humanized monoclonal antibody.

8. The isolated antibody or binding fragment of claim 4, which binds to a cancer cell expressing clathrin heavy chain (CHC).

9. The isolated antibody or binding fragment claim 4, which is labeled by a detectable compound or an enzyme.

10. The isolated antibody or binding fragment of claim 4, which is encapsulated within a liposome.

11. A method for inhibiting tumor cell growth and/or tumor angiogenesis, comprising:
administering to a subject in need thereof a composition comprising, the purified monoclonal antibody or antigen-binding portion thereof of claim 1 and a pharmaceutically acceptable carrier, wherein the tumor expresses human clathrin heavy chain.

12. A method for inhibiting tumor growth and/or tumor angiogenesis, comprising:
administering to a subject in need thereof a composition comprising the isolated monoclonal antibody, or binding fragment thereof of claim 4 and a pharmaceutically acceptable carrier, where in tumor express human clathrin heavy chain.

13. The method of claim 11, wherein the tumor cell is selected from the group consisting of pancreatic cancer cells, breast cancer cells, lung cancer cells, ovary cancer cells, oral cancer cells, and tumor-associated endothelial cells.

14. An isolated single-chain antibody comprising:
(a) the heavy chain variable region (SEQ ID NO: 2) and the light chain variable region (SEQ ID NO: 3) of the isolated antibody or binding fragment of claim 2; and
(b) a linker peptide connecting the heavy chain variable region (SEQ ID NO: 2) and the light chain variable region (SEQ ED NO: 3).

15. A composition comprising:
(a) the isolated monoclonal antibody or binding fragment of claim 4; and
(b) a pharmaceutically acceptable carrier, 16. The composition of claim 15, further comprising an anti-cancer age 17. A method for detecting cancer in a subject, comprising:
(a) applying the isolated monoclonal antibody or binding fragment thereof of claim 4 to a cell or tissue sample obtained from the subject; and
(b) assaying the binding of the isolated monoclonal antibody or binding fragment thereof to the cell or the tissue sample; and
(c) comparing the binding with a normal control to determine the presence of the cancer in the subject,
wherein the cancer expresses human clathrin heavy chain.

18. The isolated monoclonal antibody or an antigen-binding fragment thereof of claim 1, which exhibits at least one, two, three, four, five, six, seven, or all eight of the following properties:
(a) specifically binds to pancreatic adenocarcinoma cells;
(b) binds to the cell surface of cancer cells and tumor blood vessels;
(c) is internalized by CHC-expressing cells upon binding;
(d) inhibiting tumor growth, invasion, migration, and angiogenesis;
(e) inducing apoptosis in cancer cells and human umbilical vein endothelial cells (HUVECs);
(f) inhibiting tumor growth and tumor blood vessel formation in pancreatic cancer in vivo;
(g) suppressing epidermal growth factor (EGF), transferrin (Tf) and VEGF internalizations by cancer cells; and
(h) suppressing hypoxia-inucible factor-1$\alpha$ (HIF-1$\alpha$) expression and vascular endothelial growth factor (VEGF) secretion.

* * * * *

UNITED STATES PATENT AND TRADEMARK OFFICE
CERTIFICATE OF CORRECTION

PATENT NO. : 8,969,530 B2  Page 1 of 1
APPLICATION NO. : 13/644311
DATED : March 3, 2015
INVENTOR(S) : Han-Chung Wu and Kuo-Hua Tung It is certified that error appears in the above-identified patent and that said Letters Patent is hereby corrected as shown below:

In the Claims

Column 45, Line 29, Claim 1 delete "binging" and substitute --binding--
Column 46, Line 15, Claim 12 delete "antibody, or" and substitute --antibody or--
Column 46, Line 17, Claim 12 delete "carrier, where in tumor express" and substitute --carrier, wherein the tumor expresses--

Signed and Sealed this
Twenty-first Day of July, 2015

Michelle K. Lee
*Director of the United States Patent and Trademark Office*

SEQUENCE LISTING

```
<160> NUMBER OF SEQ ID NOS: 39

<210> SEQ ID NO 1
<211> LENGTH: 1675
<212> TYPE: PRT
<213> ORGANISM: Homo sapiens

<400> SEQUENCE: 1

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Val Ile Ile Asp Met Asn Asp Pro Ser Asn Pro Ile Arg Arg
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160
```

-continued

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
                180                 185                 190

Pro Ile Glu Gly His Ala Ala Ser Phe Ala Gln Phe Lys Met Glu Gly
                195                 200                 205

Asn Ala Glu Glu Ser Thr Leu Phe Cys Phe Ala Val Arg Gly Gln Ala
210                 215                 220

Gly Gly Lys Leu His Ile Ile Glu Val Gly Thr Pro Thr Gly Asn
225                 230                 235                 240

Gln Pro Phe Pro Lys Lys Ala Val Asp Val Phe Phe Pro Glu Ala
                245                 250                 255

Gln Asn Asp Phe Pro Val Ala Met Gln Ile Ser Glu Lys His Asp Val
                260                 265                 270

Val Phe Leu Ile Thr Lys Tyr Gly Tyr Ile His Leu Tyr Asp Leu Glu
                275                 280                 285

Thr Gly Thr Cys Ile Tyr Met Asn Arg Ile Ser Gly Glu Thr Ile Phe
                290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
                325                 330                 335

Tyr Ile Thr Asn Val Leu Gln Asn Pro Asp Leu Ala Leu Arg Met Ala
                340                 345                 350

Val Arg Asn Asn Leu Ala Gly Ala Glu Glu Leu Phe Ala Arg Lys Phe
                355                 360                 365

Asn Ala Leu Phe Ala Gln Gly Asn Tyr Ser Glu Ala Ala Lys Val Ala
                370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
                420                 425                 430

Leu Glu Leu Cys Arg Pro Val Leu Gln Gln Gly Arg Lys Gln Leu Leu
                435                 440                 445

Glu Lys Trp Leu Lys Glu Asp Lys Leu Glu Cys Ser Glu Glu Leu Gly
                450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
                500                 505                 510

Asp Trp Ile Phe Leu Leu Arg Asn Val Met Arg Ile Ser Pro Asp Gln
                515                 520                 525

Gly Gln Gln Phe Ala Gln Met Leu Val Gln Asp Glu Glu Pro Leu Ala
                530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala

-continued

```
              580                 585                 590
Pro Gln Val Ala Asp Ala Ile Leu Gly Asn Gln Met Phe Thr His Tyr
                595                 600                 605
Asp Arg Ala His Ile Ala Gln Leu Cys Glu Lys Ala Gly Leu Leu Gln
610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
                645                 650                 655
Ser Leu Ser Val Glu Asp Ser Leu Glu Cys Leu Arg Ala Met Leu Ser
                660                 665                 670
Ala Asn Ile Arg Gln Asn Leu Gln Ile Cys Val Gln Val Ala Ser Lys
                675                 680                 685
Tyr His Glu Gln Leu Ser Thr Gln Ser Leu Ile Glu Leu Phe Glu Ser
                690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
                725                 730                 735
Lys Thr Gly Gln Ile Lys Glu Val Glu Arg Ile Cys Arg Glu Ser Asn
                740                 745                 750
Cys Tyr Asp Pro Glu Arg Val Lys Asn Phe Leu Lys Glu Ala Lys Leu
                755                 760                 765
Thr Asp Gln Leu Pro Leu Ile Ile Val Cys Asp Arg Phe Asp Phe Val
                770                 775                 780
His Asp Leu Val Leu Tyr Leu Tyr Arg Asn Asn Leu Gln Lys Tyr Ile
785                 790                 795                 800
Glu Ile Tyr Val Gln Lys Val Asn Pro Ser Arg Leu Pro Val Val Ile
                805                 810                 815
Gly Gly Leu Leu Asp Val Asp Cys Ser Glu Asp Val Ile Lys Asn Leu
                820                 825                 830
Ile Leu Val Val Arg Gly Gln Phe Ser Thr Asp Glu Leu Val Ala Glu
                835                 840                 845
Val Glu Lys Arg Asn Arg Leu Lys Leu Leu Leu Pro Trp Leu Glu Ala
                850                 855                 860
Arg Ile His Glu Gly Cys Glu Glu Pro Ala Thr His Asn Ala Leu Ala
865                 870                 875                 880
Lys Ile Tyr Ile Asp Ser Asn Asn Asn Pro Glu Arg Phe Leu Arg Glu
                885                 890                 895
Asn Pro Tyr Tyr Asp Ser Arg Val Val Gly Lys Tyr Cys Glu Lys Arg
                900                 905                 910
Asp Pro His Leu Ala Cys Val Ala Tyr Glu Arg Gly Gln Cys Asp Leu
                915                 920                 925
Glu Leu Ile Asn Val Cys Asn Glu Asn Ser Leu Phe Lys Ser Leu Ser
                930                 935                 940
Arg Tyr Leu Val Arg Arg Lys Asp Pro Glu Leu Trp Gly Ser Val Leu
945                 950                 955                 960
Leu Glu Ser Asn Pro Tyr Arg Arg Pro Leu Ile Asp Gln Val Val Gln
                965                 970                 975
Thr Ala Leu Ser Glu Thr Gln Asp Pro Glu Glu Val Ser Val Thr Val
                980                 985                 990
Lys Ala Phe Met Thr Ala Asp Leu Pro Asn Glu Leu Ile Glu Leu Leu
                995                 1000                1005
```

```
Glu Lys Ile Val Leu Asp Asn Ser Val Phe Ser Glu His Arg Asn
    1010                1015            1020

Leu Gln Asn Leu Leu Ile Leu Thr Ala Ile Lys Ala Asp Arg Thr
    1025                1030            1035

Arg Val Met Glu Tyr Ile Asn Arg Leu Asp Asn Tyr Asp Ala Pro
    1040                1045            1050

Asp Ile Ala Asn Ile Ala Ile Ser Asn Glu Leu Phe Glu Glu Ala
    1055                1060            1065

Phe Ala Ile Phe Arg Lys Phe Asp Val Asn Thr Ser Ala Val Gln
    1070                1075            1080

Val Leu Ile Glu His Ile Gly Asn Leu Asp Arg Ala Tyr Glu Phe
    1085                1090            1095

Ala Glu Arg Cys Asn Glu Pro Ala Val Trp Ser Gln Leu Ala Lys
    1100                1105            1110

Ala Gln Leu Gln Lys Gly Met Val Lys Glu Ala Ile Asp Ser Tyr
    1115                1120            1125

Ile Lys Ala Asp Asp Pro Ser Ser Tyr Met Glu Val Val Gln Ala
    1130                1135            1140

Ala Asn Thr Ser Gly Asn Trp Glu Glu Leu Val Lys Tyr Leu Gln
    1145                1150            1155

Met Ala Arg Lys Lys Ala Arg Glu Ser Tyr Val Glu Thr Glu Leu
    1160                1165            1170

Ile Phe Ala Leu Ala Lys Thr Asn Arg Leu Ala Glu Leu Glu Glu
    1175                1180            1185

Phe Ile Asn Gly Pro Asn Asn Ala His Ile Gln Gln Val Gly Asp
    1190                1195            1200

Arg Cys Tyr Asp Glu Lys Met Tyr Asp Ala Ala Lys Leu Leu Tyr
    1205                1210            1215

Asn Asn Val Ser Asn Phe Gly Arg Leu Ala Ser Thr Leu Val His
    1220                1225            1230

Leu Gly Glu Tyr Gln Ala Ala Val Asp Gly Ala Arg Lys Ala Asn
    1235                1240            1245

Ser Thr Arg Thr Trp Lys Glu Val Cys Phe Ala Cys Val Asp Gly
    1250                1255            1260

Lys Glu Phe Arg Leu Ala Gln Met Cys Gly Leu His Ile Val Val
    1265                1270            1275

His Ala Asp Glu Leu Glu Glu Leu Ile Asn Tyr Tyr Gln Asp Arg
    1280                1285            1290

Gly Tyr Phe Glu Glu Leu Ile Thr Met Leu Glu Ala Ala Leu Gly
    1295                1300            1305

Leu Glu Arg Ala His Met Gly Met Phe Thr Glu Leu Ala Ile Leu
    1310                1315            1320

Tyr Ser Lys Phe Lys Pro Gln Lys Met Arg Glu His Leu Glu Leu
    1325                1330            1335

Phe Trp Ser Arg Val Asn Ile Pro Lys Val Leu Arg Ala Ala Glu
    1340                1345            1350

Gln Ala His Leu Trp Ala Glu Leu Val Phe Leu Tyr Asp Lys Tyr
    1355                1360            1365

Glu Glu Tyr Asp Asn Ala Ile Ile Thr Met Met Asn His Pro Thr
    1370                1375            1380

Asp Ala Trp Lys Glu Gly Gln Phe Lys Asp Ile Ile Thr Lys Val
    1385                1390            1395
```

```
Ala Asn Val Glu Leu Tyr Tyr Arg Ala Ile Gln Phe Tyr Leu Glu
    1400                1405                1410

Phe Lys Pro Leu Leu Leu Asn Asp Leu Leu Met Val Leu Ser Pro
    1415                1420                1425

Arg Leu Asp His Thr Arg Ala Val Asn Tyr Phe Ser Lys Val Lys
    1430                1435                1440

Gln Leu Pro Leu Val Lys Pro Tyr Leu Arg Ser Val Gln Asn His
    1445                1450                1455

Asn Asn Lys Ser Val Asn Glu Ser Leu Asn Asn Leu Phe Ile Thr
    1460                1465                1470

Glu Glu Asp Tyr Gln Ala Leu Arg Thr Ser Ile Asp Ala Tyr Asp
    1475                1480                1485

Asn Phe Asp Asn Ile Ser Leu Ala Gln Arg Leu Glu Lys His Glu
    1490                1495                1500

Leu Ile Glu Phe Arg Arg Ile Ala Ala Tyr Leu Phe Lys Gly Asn
    1505                1510                1515

Asn Arg Trp Lys Gln Ser Val Glu Leu Cys Lys Lys Asp Ser Leu
    1520                1525                1530

Tyr Lys Asp Ala Met Gln Tyr Ala Ser Glu Ser Lys Asp Thr Glu
    1535                1540                1545

Leu Ala Glu Glu Leu Leu Gln Trp Phe Leu Gln Glu Glu Lys Arg
    1550                1555                1560

Glu Cys Phe Gly Ala Cys Leu Phe Thr Cys Tyr Asp Leu Leu Arg
    1565                1570                1575

Pro Asp Val Val Leu Glu Thr Ala Trp Arg His Asn Ile Met Asp
    1580                1585                1590

Phe Ala Met Pro Tyr Phe Ile Gln Val Met Lys Glu Tyr Leu Thr
    1595                1600                1605

Lys Val Asp Lys Leu Asp Ala Ser Glu Ser Leu Arg Lys Glu Glu
    1610                1615                1620

Glu Gln Ala Thr Glu Thr Gln Pro Ile Val Tyr Gly Gln Pro Gln
    1625                1630                1635

Leu Met Leu Thr Ala Gly Pro Ser Val Ala Val Pro Pro Gln Ala
    1640                1645                1650

Pro Phe Gly Tyr Gly Tyr Thr Ala Pro Pro Tyr Gly Gln Pro Gln
    1655                1660                1665

Pro Gly Phe Gly Tyr Ser Met
    1670                1675

<210> SEQ ID NO 2
<211> LENGTH: 133
<212> TYPE: PRT
<213> ORGANISM: Homo sapiens

<400> SEQUENCE: 2

Glu Val Lys Leu Val Glu Ser Gly Gly Gly Leu Val Lys Pro Gly Gly
 1               5                  10                  15

Ser Leu Asn Ile Ser Cys Ala Ala Ser Gly Phe Thr Phe Ser Asn Tyr
                20                  25                  30

Val Met Ser Trp Val Arg Gln Thr Pro Glu Lys Arg Leu Glu Trp Val
            35                  40                  45

Ala Thr Ile Ser Ser Gly Asp Asn Tyr Met Tyr Tyr Pro Asp Ser Val
        50                  55                  60

Lys Gly Arg Phe Thr Ile Ser Ser Asp Asn Ala Lys Asn Thr Leu Phe
65                  70                  75                  80
```

```
Leu Gln Met Ser Ser Leu Arg Ser Glu Asp Thr Ala Leu Tyr Tyr Cys
                85                  90                  95

Ala Arg His Phe Asp Asn Tyr Glu Gly Asn Ser Met Asp Tyr Trp Gly
            100                 105                 110

Gln Gly Thr Ser Val Thr Val Ser Ser Ala Lys Thr Thr Pro Pro Ser
        115                 120                 125

Asp Tyr Pro Leu Ala
    130

<210> SEQ ID NO 3
<211> LENGTH: 116
<212> TYPE: PRT
<213> ORGANISM: Homo sapiens

<400> SEQUENCE: 3

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Arg Ser Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Ile Leu Ser Ile Asn Ser Val Ala Thr
65                  70                  75                  80

Glu Asp Phe Gly Val Tyr Phe Cys Gln Gln Ser Asn Ser Trp Pro Leu
                85                  90                  95

Thr Phe Gly Ala Gly Thr Lys Leu Glu Leu Lys Arg Ala Asp Ala Ala
            100                 105                 110

Pro Thr Val Ser
        115

<210> SEQ ID NO 4
<211> LENGTH: 5
<212> TYPE: PRT
<213> ORGANISM: Homo sapiens

<400> SEQUENCE: 4

Asn Tyr Val Met Ser
1               5

<210> SEQ ID NO 5
<211> LENGTH: 17
<212> TYPE: PRT
<213> ORGANISM: Homo sapiens

<400> SEQUENCE: 5

Thr Ile Ser Ser Gly Asp Asn Tyr Met Tyr Tyr Pro Asp Ser Val Lys
1               5                   10                  15

Gly

<210> SEQ ID NO 6
<211> LENGTH: 12
<212> TYPE: PRT
<213> ORGANISM: Homo sapiens

<400> SEQUENCE: 6

His Phe Asp Asn Tyr Glu Gly Asn Ser Met Asp Tyr
1               5                   10
```

<210> SEQ ID NO 7
<211> LENGTH: 11
<212> TYPE: PRT
<213> ORGANISM: Homo sapiens

<400> SEQUENCE: 7

Arg Ala Ser Gln Ser Ile Arg Ser Asn Leu His
1               5                   10

<210> SEQ ID NO 8
<211> LENGTH: 7
<212> TYPE: PRT
<213> ORGANISM: Homo sapiens

<400> SEQUENCE: 8

Tyr Ala Ser Gln Ser Ile Ser
1               5

<210> SEQ ID NO 9
<211> LENGTH: 8
<212> TYPE: PRT
<213> ORGANISM: Homo sapiens

<400> SEQUENCE: 9

Gln Gln Ser Asn Ser Trp Pro Leu
1               5

<210> SEQ ID NO 10
<211> LENGTH: 30
<212> TYPE: PRT
<213> ORGANISM: Homo sapiens

<400> SEQUENCE: 10

Glu Val Lys Leu Val Glu Ser Gly Gly Gly Leu Val Lys Pro Gly Gly
1               5                   10                  15

Ser Leu Asn Ile Ser Cys Ala Ala Ser Gly Phe Thr Phe Ser
            20                  25                  30

<210> SEQ ID NO 11
<211> LENGTH: 14
<212> TYPE: PRT
<213> ORGANISM: Homo sapiens

<400> SEQUENCE: 11

Trp Val Arg Gln Thr Pro Glu Lys Arg Leu Glu Trp Val Ala
1               5                   10

<210> SEQ ID NO 12
<211> LENGTH: 32
<212> TYPE: PRT
<213> ORGANISM: Homo sapiens

<400> SEQUENCE: 12

Arg Phe Thr Ile Ser Ser Asp Asn Ala Lys Asn Thr Leu Phe Leu Gln
1               5                   10                  15

Met Ser Ser Leu Arg Ser Glu Asp Thr Ala Leu Tyr Tyr Cys Ala Arg
            20                  25                  30

<210> SEQ ID NO 13
<211> LENGTH: 23
<212> TYPE: PRT
<213> ORGANISM: Homo sapiens

<400> SEQUENCE: 13

Trp Gly Gln Gly Thr Ser Val Thr Val Ser Ser Ala Lys Thr Thr Pro
1               5                   10                  15

Pro Ser Asp Tyr Pro Leu Ala
            20

<210> SEQ ID NO 14
<211> LENGTH: 23
<212> TYPE: PRT
<213> ORGANISM: Homo sapiens

<400> SEQUENCE: 14

Asp Ile Val Leu Thr Gln Ser Pro Ala Thr Leu Ser Val Thr Pro Gly
1               5                   10                  15

Asp Ser Val Ser Leu Ser Cys
            20

<210> SEQ ID NO 15
<211> LENGTH: 15
<212> TYPE: PRT
<213> ORGANISM: Homo sapiens

<400> SEQUENCE: 15

Trp Tyr Gln Gln Lys Ser His Glu Ser Pro Arg Leu Leu Ile Lys
1               5                   10                  15

<210> SEQ ID NO 16
<211> LENGTH: 32
<212> TYPE: PRT
<213> ORGANISM: Homo sapiens

<400> SEQUENCE: 16

Gly Ile Pro Ser Arg Phe Ser Gly Ser Gly Ser Gly Thr Asp Phe Ile
1               5                   10                  15

Leu Ser Ile Asn Ser Val Ala Thr Glu Asp Phe Gly Val Tyr Phe Cys
            20                  25                  30

<210> SEQ ID NO 17
<211> LENGTH: 20
<212> TYPE: PRT
<213> ORGANISM: Homo sapiens

<400> SEQUENCE: 17

Thr Phe Gly Ala Gly Thr Lys Leu Glu Leu Lys Arg Ala Asp Ala Ala
1               5                   10                  15

Pro Thr Val Ser
            20

<210> SEQ ID NO 18
<211> LENGTH: 28
<212> TYPE: DNA
<213> ORGANISM: Artificial Sequence
<220> FEATURE:
<223> OTHER INFORMATION: Cloning VEGF f

<400> SEQUENCE: 18
ggtaccgggc cacggagtga ctggtgat                                  28

<210> SEQ ID NO 19
<211> LENGTH: 32
<212> TYPE: DNA
<213> ORGANISM: Artificial Sequence
<220> FEATURE:

<223> OTHER INFORMATION: Cloning VEGF r

<400> SEQUENCE: 19
ctcgagggaa gagagagacg gggtcagaga ga                            32

<210> SEQ ID NO 20
<211> LENGTH: 24
<212> TYPE: DNA
<213> ORGANISM: Artificial Sequence
<220> FEATURE:
<223> OTHER INFORMATION: RT-PCR CLTC f

<400> SEQUENCE: 20
gacaaaggtg gataaattag atgc                                     24

<210> SEQ ID NO 21
<211> LENGTH: 24
<212> TYPE: DNA
<213> ORGANISM: Artificial Sequence
<220> FEATURE:
<223> OTHER INFORMATION: RT-PCR CLTC r

<400> SEQUENCE: 21
taaacaatgg gttgtgtctc tgta                                     24

<210> SEQ ID NO 22
<211> LENGTH: 19
<212> TYPE: DNA
<213> ORGANISM: Artificial Sequence
<220> FEATURE:
<223> OTHER INFORMATION: RT-PCR VEGF f

<400> SEQUENCE: 22
acatcttcca ggagtaccc                                           19

<210> SEQ ID NO 23
<211> LENGTH: 19
<212> TYPE: DNA
<213> ORGANISM: Artificial Sequence
<220> FEATURE:
<223> OTHER INFORMATION: RT-PCR VEGf r

<400> SEQUENCE: 23
cttggtgagg tttgatccg                                           19

<210> SEQ ID NO 24
<211> LENGTH: 23
<212> TYPE: DNA
<213> ORGANISM: Artificial Sequence
<220> FEATURE:
<223> OTHER INFORMATION: RT-PCR HIF-1alpha  f

<400> SEQUENCE: 24
ggttcacttt ttcaagcagt agg                                      23

<210> SEQ ID NO 25
<211> LENGTH: 23
<212> TYPE: DNA
<213> ORGANISM: Artificial Sequence
<220> FEATURE:
<223> OTHER INFORMATION: RT-PCR HIF-1alpha  r

<400> SEQUENCE: 25
gtggtaatcc actttcatcc att                                      23

```
<210> SEQ ID NO 26
<211> LENGTH: 19
<212> TYPE: DNA
<213> ORGANISM: Artificial Sequence
<220> FEATURE:
<223> OTHER INFORMATION: RT-PCR EPO f

<400> SEQUENCE: 26
agcaggaagc attcagaga                                               19

<210> SEQ ID NO 27
<211> LENGTH: 19
<212> TYPE: DNA
<213> ORGANISM: Artificial Sequence
<220> FEATURE:
<223> OTHER INFORMATION: RT-PCR EPO r

<400> SEQUENCE: 27
aggtaaatcg cctccaaag                                               19

<210> SEQ ID NO 28
<211> LENGTH: 20
<212> TYPE: DNA
<213> ORGANISM: Artificial Sequence
<220> FEATURE:
<223> OTHER INFORMATION: RT-PCR PDGF-beta  f

<400> SEQUENCE: 28
ctggcatgca agtgtgagac                                              20

<210> SEQ ID NO 29
<211> LENGTH: 19
<212> TYPE: DNA
<213> ORGANISM: Artificial Sequence
<220> FEATURE:
<223> OTHER INFORMATION: RT-PCR PDGF-beta  r

<400> SEQUENCE: 29
cgaatggtca cccgagttt                                               19

<210> SEQ ID NO 30
<211> LENGTH: 21
<212> TYPE: DNA
<213> ORGANISM: Artificial Sequence
<220> FEATURE:
<223> OTHER INFORMATION: RT-PCR GAPDH f

<400> SEQUENCE: 30
cttcaccacc atggaggagg c                                            21

<210> SEQ ID NO 31
<211> LENGTH: 21
<212> TYPE: DNA
<213> ORGANISM: Artificial Sequence
<220> FEATURE:
<223> OTHER INFORMATION: RT-PCR GAPDH r

<400> SEQUENCE: 31
ggcatggact gtggtcatga g                                            21

<210> SEQ ID NO 32
<211> LENGTH: 17
<212> TYPE: DNA
<213> ORGANISM: Artificial Sequence
<220> FEATURE:
<223> OTHER INFORMATION: ChIP VEGF f
```

<400> SEQUENCE: 32
gagcccgcgc ccggagg                                                    17

<210> SEQ ID NO 33
<211> LENGTH: 17
<212> TYPE: DNA
<213> ORGANISM: Artificial Sequence
<220> FEATURE:
<223> OTHER INFORMATION: ChIP VEGF r

<400> SEQUENCE: 33
cagcccagaa gttggac                                                    17

<210> SEQ ID NO 34
<211> LENGTH: 20
<212> TYPE: DNA
<213> ORGANISM: Artificial Sequence
<220> FEATURE:
<223> OTHER INFORMATION: ChIP GAPDH f

<400> SEQUENCE: 34
aggtgaaggt cggagtcaac                                                 20

<210> SEQ ID NO 35
<211> LENGTH: 20
<212> TYPE: DNA
<213> ORGANISM: Artificial Sequence
<220> FEATURE:
<223> OTHER INFORMATION: ChIP GAPDH r

<400> SEQUENCE: 35
tcttctgggt ggcagtgatg                                                 20

<210> SEQ ID NO 36
<211> LENGTH: 34
<212> TYPE: DNA
<213> ORGANISM: Artificial Sequence
<220> FEATURE:
<223> OTHER INFORMATION: VH1FOR

<400> SEQUENCE: 36
tgaggagacg gtgaccgtgg tcccttggcc ccag                                 34

<210> SEQ ID NO 37
<211> LENGTH: 22
<212> TYPE: DNA
<213> ORGANISM: Artificial Sequence
<220> FEATURE:
<223> OTHER INFORMATION: VK1FOR

<400> SEQUENCE: 37
gttagatctc cagcttggtc cc                                              22

<210> SEQ ID NO 38
<211> LENGTH: 22
<212> TYPE: DNA
<213> ORGANISM: Artificial Sequence
<220> FEATURE:
<223> OTHER INFORMATION: VH1BACK

<400> SEQUENCE: 38
aggtcaaact gcagsagtca gg                                              22

<210> SEQ ID NO 39
<211> LENGTH: 24

```
<212> TYPE: DNA
<213> ORGANISM: Artificial Sequence
<220> FEATURE:
<223> OTHER INFORMATION: VK1BACK

<400> SEQUENCE: 39
gacattcagc tgacccagtc tcca                                              24
```